US011375959B2

(12) United States Patent
Toth et al.

(10) Patent No.: US 11,375,959 B2
(45) Date of Patent: Jul. 5, 2022

(54) CONTINUOUS LONG-TERM MONITORING OF A SUBJECT

(71) Applicant: LifeLens Technologies, LLC, Ivyland, PA (US)

(72) Inventors: Landy Toth, Doylestown, PA (US); Robert S. Schwartz, Inver Grove Heights, MN (US)

(73) Assignee: LifeLens Technologies, LLC, Ivyland, PA (US)

( * ) Notice: Subject to any disclaimer, the term of this patent is extended or adjusted under 35 U.S.C. 154(b) by 221 days.

(21) Appl. No.: 16/463,127

(22) PCT Filed: Nov. 20, 2017

(86) PCT No.: PCT/US2017/062539
§ 371 (c)(1),
(2) Date: May 22, 2019

(87) PCT Pub. No.: WO2018/098073
PCT Pub. Date: May 31, 2018

(65) Prior Publication Data
US 2019/0290208 A1    Sep. 26, 2019

Related U.S. Application Data

(60) Provisional application No. 62/425,994, filed on Nov. 23, 2016.

(51) Int. Cl.
*A61B 5/00*    (2006.01)
*A61B 5/01*    (2006.01)
(Continued)

(52) U.S. Cl.
CPC .............. *A61B 5/7246* (2013.01); *A61B 5/00* (2013.01); *A61B 5/01* (2013.01); *A61B 5/02* (2013.01);
(Continued)

(58) Field of Classification Search
CPC ..... A61B 5/7246; A61B 5/318; A61B 5/7203; A61B 5/02; A61B 5/6833
See application file for complete search history.

(56) References Cited

U.S. PATENT DOCUMENTS

2011/0288379 A1    11/2011  Wu
2015/0335288 A1*   11/2015  Toth ..................... A61B 5/6833
                                                                600/373
(Continued)

FOREIGN PATENT DOCUMENTS

WO         2009038768 A1    3/2009
WO         2017190049 A1    11/2017
WO  PCT/US2017/062539       1/2018

OTHER PUBLICATIONS

Extended European Search Report for European Application Serial No. 17873538, filed Jun. 17, 2020.
(Continued)

*Primary Examiner* — Paula J Stice
(74) *Attorney, Agent, or Firm* — Ryan, Mason & Lewis, LLP

(57) ABSTRACT

A method includes obtaining monitoring data recorded by first and second devices, the first and second devices being attached to the subject at different first and second sties, respectively. The monitoring data comprises signals associated with at least one physiological parameter of the subject. The method also includes extracting one or more features of the signals recorded by the first and second devices during a transitionary period when the first and second devices simultaneously monitor the at least one physiological parameter of the subject. The method further includes generating at least one correlation parameter by analyzing the extracted features of the signals recorded by the first and second devices for at least a portion of the transitionary period, the at least one correlation parameter when applied
(Continued)

to signals recorded by the second device at least partially compensating for relative changes in signals recorded by the first and second devices.

20 Claims, 19 Drawing Sheets

(51) Int. Cl.
    *A61B 5/0537*     (2021.01)
    *A61B 5/02*     (2006.01)
    *A61B 5/0205*     (2006.01)
    *A61B 5/11*     (2006.01)
    *A61B 5/318*     (2021.01)
    *A61B 5/389*     (2021.01)
    *A61B 5/145*     (2006.01)
    *A61B 5/24*     (2021.01)

(52) U.S. Cl.
    CPC .......... *A61B 5/0205* (2013.01); *A61B 5/0537* (2013.01); *A61B 5/11* (2013.01); *A61B 5/318* (2021.01); *A61B 5/389* (2021.01); *A61B 5/6833* (2013.01); *A61B 5/7203* (2013.01); *A61B 5/74* (2013.01); *A61B 5/14517* (2013.01); *A61B 5/24* (2021.01); *A61B 5/6839* (2013.01); *A61B 5/6843* (2013.01); *A61B 5/6844* (2013.01); *A61B 2560/04* (2013.01); *A61B 2562/0219* (2013.01); *A61B 2562/0247* (2013.01); *A61B 2562/0271* (2013.01); *A61B 2562/164* (2013.01); *A61B 2562/166* (2013.01); *A61B 2562/18* (2013.01)

(56) References Cited

U.S. PATENT DOCUMENTS

2016/0000360 A1    1/2016    Feldman
2016/0302674 A1    10/2016    Moyer et al.
2017/0027513 A1    2/2017    Mulpuru

OTHER PUBLICATIONS

India Application No. 201947020404 filed on May 23, 2019, Examination Report dated Sep. 12, 2021.

* cited by examiner

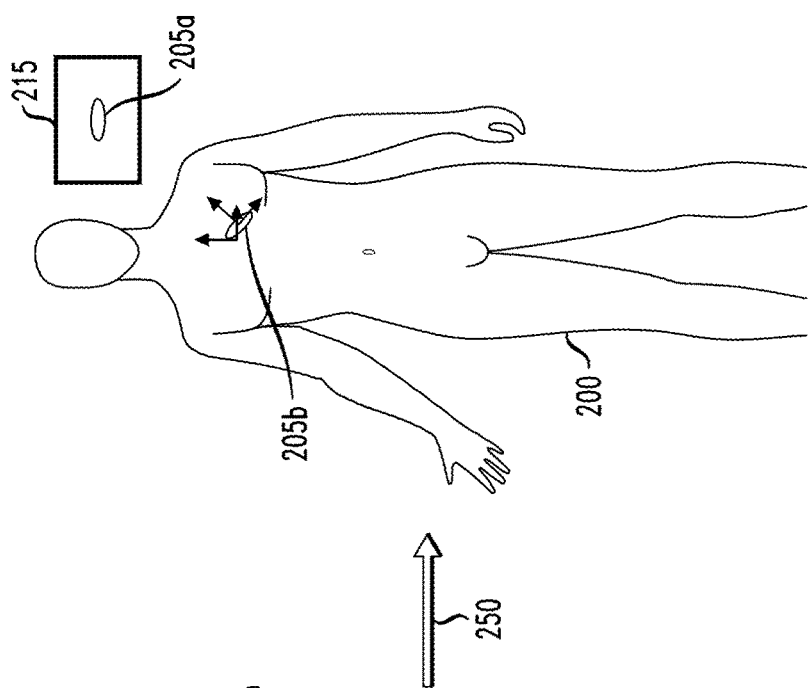
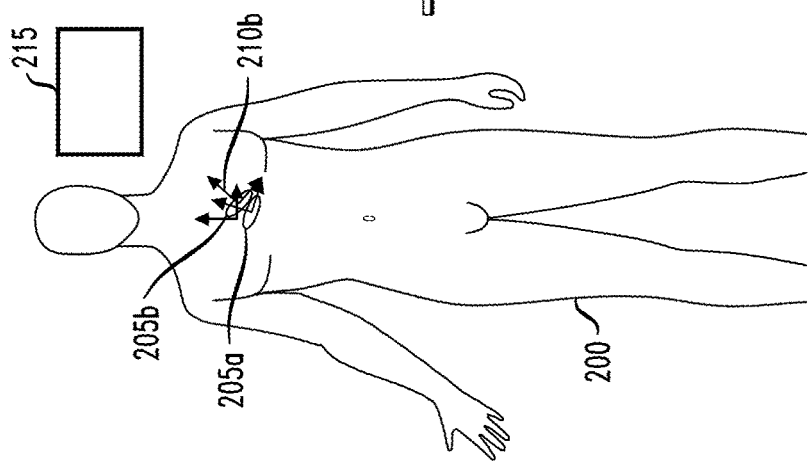
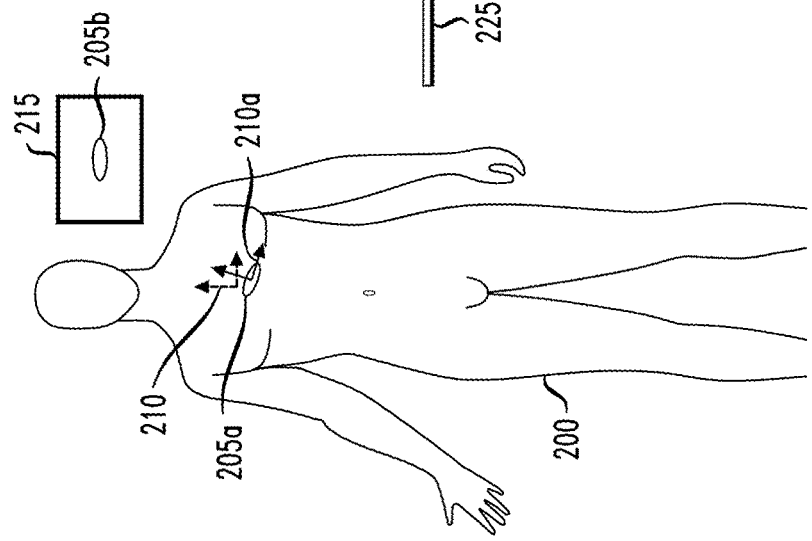

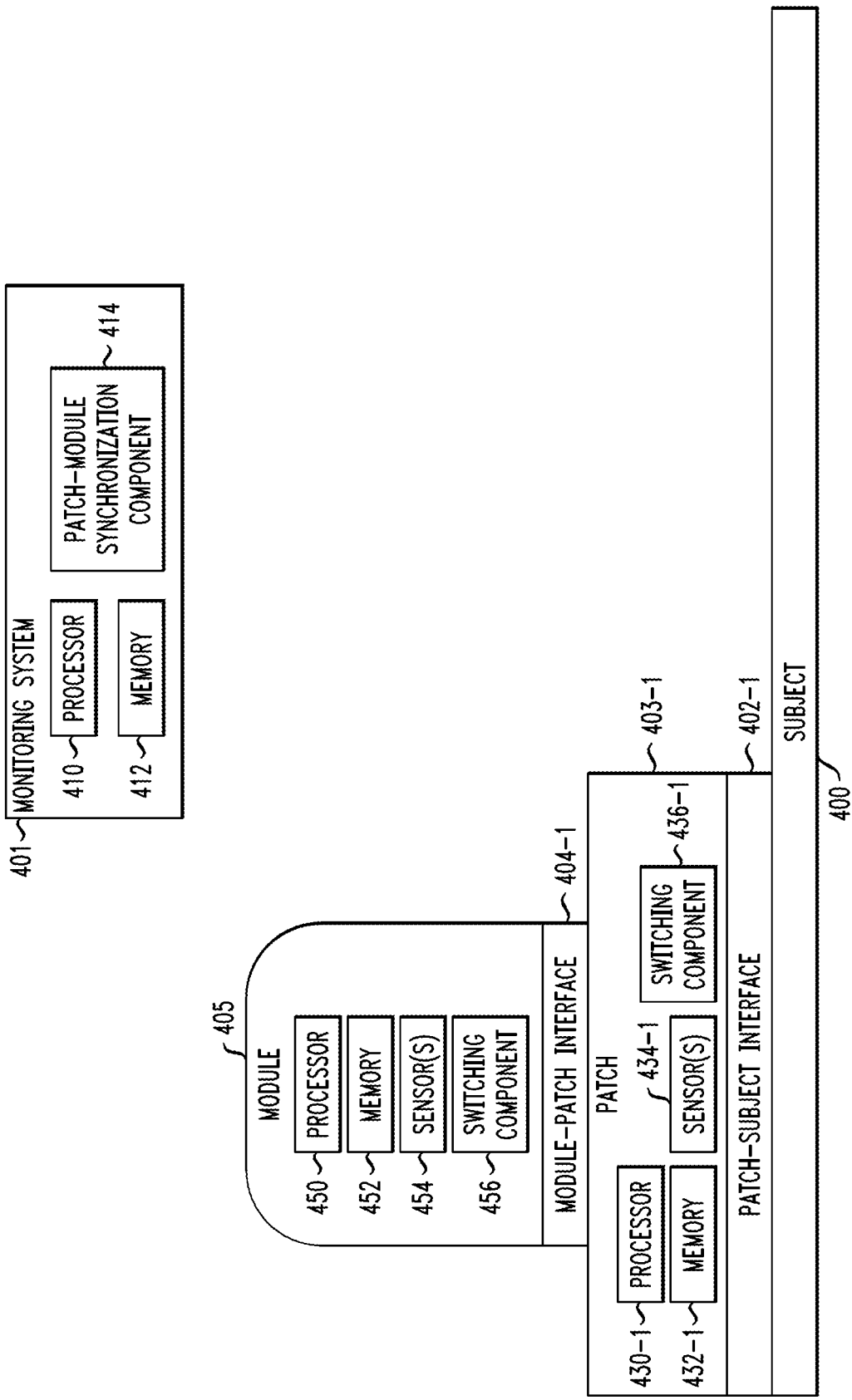

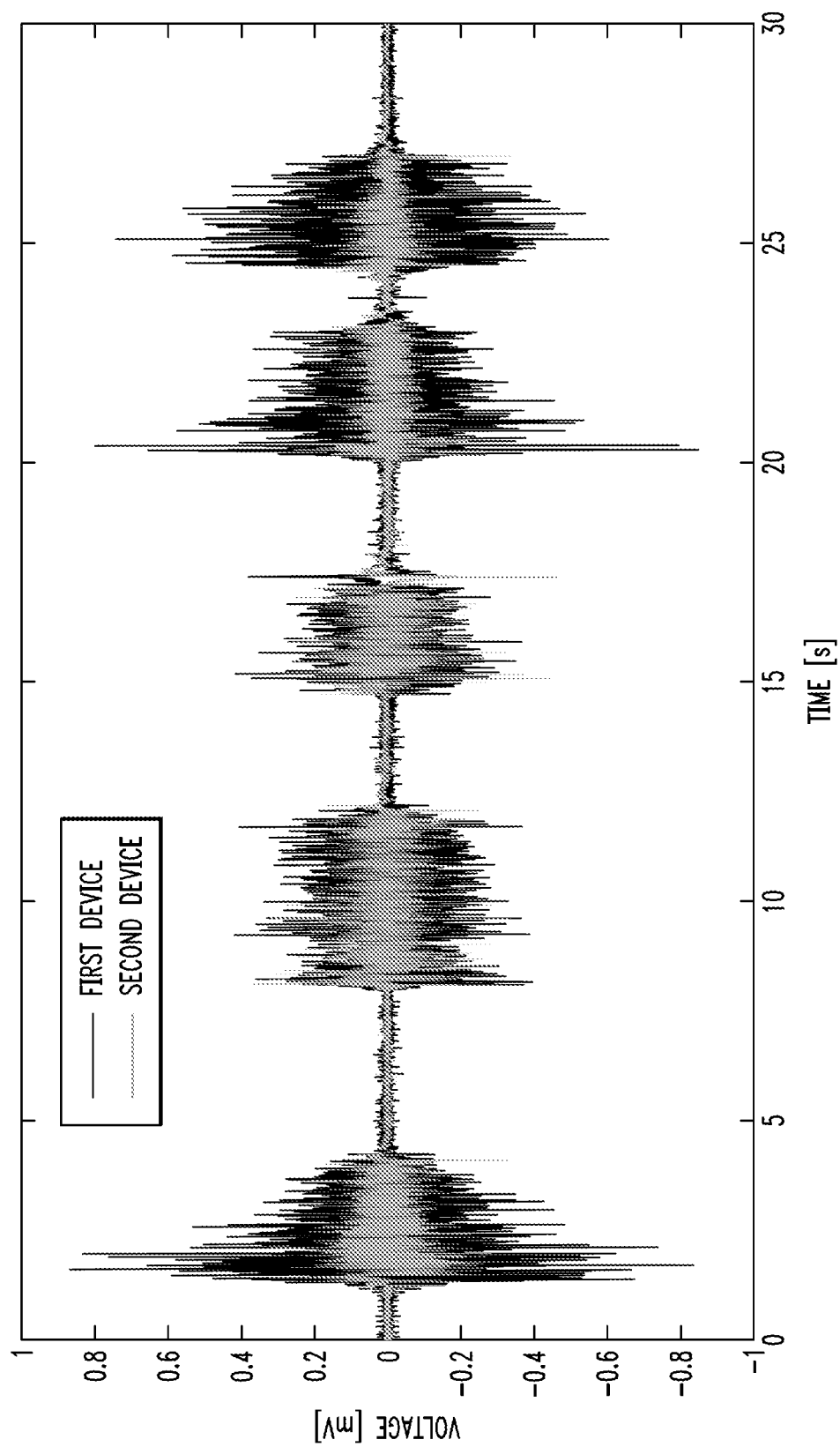

CONTINUOUS LONG-TERM MONITORING OF A SUBJECT

TECHNICAL FIELD

The present disclosure relates to the field of physiologic monitoring and, more particularly, to devices and systems for reliable measurement and unobtrusive monitoring of a subject.

BACKGROUND

As chronic diseases continue to proliferate throughout the world, there is a heightened need to treat such conditions in a cost effective manner. Remote monitoring of patients with cardiovascular diseases (heart failure, post stroke, etc.), diabetes, kidney failure, COPD, obesity, neurological disorders (depression, Alzheimer's disease, migraines, stress disorders, etc.), arthritis, among other ailments, for purposes of treatment or prevention of such diseases may substantially improve patient outcomes.

Although physiologic monitoring is performed today for a range of purposes, existing technologies are not without shortcomings.

There is a need to measure physiologic parameters of subjects, reliably, simply, and without cables. As the proliferation of mobile and remote medicine increases, simplified and unobtrusive means for monitoring the physiologic parameters of a patient become more important.

Patient compliance is critical to the success of such systems and is often directly correlated to the ease of use and unobtrusiveness of the monitoring solution used.

Existing monitoring systems are often prone to false alarms, usage related failures, unreliable user interfaces, cumbersome interfaces, artifact or electromagnetic interference (EMI) related interference, etc. Such problems decrease productivity of using these systems, can result in lost data, and lead to dissatisfaction on the part of both the subject being monitored and the practitioners monitoring the subject. In the case of a hospital setting, the continual drone of alarms can lead to alarm fatigue and decreased productivity.

Long term compliance of subjects may suffer due to uncomfortable interfaces with monitoring devices, involved maintenance or change-over of disposables, painful or itchy reactions to materials in the devices, and the like.

More reliable, redundant, and user friendly systems are needed that can provide valuable patient data even when operating with limited supervision, expert input, or user manipulation.

SUMMARY

One illustrative, non-limiting objective of this disclosure is to provide systems, devices, methods, and kits for monitoring physiologic and/or physical signals from a subject. Another illustrative, non-limiting objective is to provide simplified systems for monitoring subjects. Another illustrative, non-limiting objective is to provide comfortable long term wearable systems for monitoring subjects. Yet another illustrative, non-limiting objective is to provide systems for facilitating interaction between a user and a subject with regard to physiologic monitoring of the subject.

The above illustrative, non-limiting objectives are wholly or partially met by devices, systems, and methods according to the appended claims in accordance with the present disclosure. Features and aspects are set forth in the appended claims, in the following description, and in the annexed drawings in accordance with the present disclosure.

In one embodiment, In one embodiment, a method comprises obtaining monitoring data recorded by a first device and at least a second device, the first device being attached to a subject at a first site and the second device being attached to the subject at a second site different than the first site, the monitoring data comprising one or more signals associated with at least one physiological parameter of the subject.

The method also comprises extracting, from the monitored data, one or more features of signals recorded by the first device and the second device during a transitionary period when the first device and the second device are simultaneously monitoring said at least one physiological parameter of the subject. The method further comprises generating at least one correlation parameter by analyzing the one or more extracted features of the signals recorded by the first device and the second device for at least a portion of the transitionary period, said at least one correlation parameter when applied to signals recorded by at least one of the first device and the second device at least partially compensating for changes in signals recorded by the first device and the second device relative to one another. The method further comprises applying said at least one correlation parameter to signals recorded by the second device. The method is performed by at least one processing device comprising a processor coupled to a memory.

In some embodiments, said at least one correlation parameter calibrates the first device and the second device to one another. Calibrating the first device and the second device to one another may comprise adjusting one or more of the features of the signals recorded by the first device and the second device to a mean of the features of the signals recorded by the first device and the second device. In some embodiments, extracting the one or more features of the signals recorded by the first device and the second device comprises determining noise profiles of the first device and the second device, and calibrating the first device and the second device to one another comprises adjusting signals recorded by the first device and the second device to the device having the lower noise profile.

In some embodiments, the first device and the second device are part of a plurality of devices attached to the subject. The plurality of devices, including the first device and the second device, may provide redundant monitoring of said at least one physiological parameter of the subject, may analyze said at least one physiological parameter of the subject from two or more different perspectives, may provide for higher order functionality in monitoring of said at least one physiological parameter of the subject relative to monitoring using fewer than all of the plurality of devices, or the like. The higher order functionality may comprise providing improved estimates of said at least one physiological parameter of the subject, providing gradient estimates of said at least one physiological parameter of the subject (e.g., such as gradient estimates for water load distribution, heat flux, etc.), providing a higher order electrocardiogram of the subject, providing a higher order electromyography readings of the subject, etc.

In some embodiments, two or more of the plurality of devices monitor different physiological parameters of the subject.

In some embodiments, a first subset of the plurality of devices monitors a given physiological parameter of the subject at a first location and a second subset of the plurality of devices monitors the given physiological parameter of the subject at a second location different than the first location.

In some embodiments, a first subset of the plurality of devices monitors a first physiological parameter of the subject at a first location and a second subset of the plurality of devices monitors a second physiological parameter of the subject at a second location, wherein the first physiological parameter and the second physiological parameter are different but related to one another. Said at least one correlation parameter may account for timing differences between signals recorded by the first subset of the plurality of device and the signals recorded by the second subset of the plurality of devices. The first subset of the plurality of devices may monitor an electrocardiogram on the chest of the subject and the second subset of the plurality of devices may monitor a pulse on an extremity of the subject away from the chest of the subject.

In some embodiments, the first device and the second device provide uninterrupted monitoring of said at least one physiological parameter of the subject over a continuous monitoring period in which at least one of the first device and the second device is not attached to the subject for at least a portion of the continuous monitoring period.

In some embodiments, the method further includes attaching the first device to the subject at the first site, monitoring said at least one physiological parameter of the subject utilizing the first device for a first monitoring period prior to the transitionary period, attaching the second device to the subject at the second site, monitoring said at least one physiological parameter of the subject utilizing the first device and the second device during the transitionary period, removing the first device from the subject following the transitionary period, and monitoring said at least one physiological parameter of the subject utilizing the second device during a second monitoring period subsequent to the transitionary period, wherein said at least one correlation parameter is applied to signals recorded by the second device during the second monitoring period.

In some embodiments, attaching the second device to the subject at the second site is responsive to detecting one or more triggering conditions associated with the first device. The one or more triggering conditions may comprise one or more of detecting a designated failure condition in the first device, detecting that a battery level of the first device is below a designated threshold, detecting that upgraded hardware is available, detecting expiration of a designated time period, and detecting a user request to initiate swapping of the first device.

In some embodiments, the second site is within a threshold distance of the first site. The threshold distance may be less than 50 millimeters.

In some embodiments, the first site and the second site are within a threshold distance of a desired monitoring site. The threshold distance may be less than 50 millimeters.

In some embodiments, the method further comprises attaching the first device to the subject at the first site, monitoring said at least one physiological parameter of the subject utilizing the first device for a first monitoring period prior to transitionary period, attaching the second device to the subject at the second site, monitoring said at least one physiological parameter of the subject utilizing the first device and the second device during the transitionary period, and monitoring said at least one physiological parameter of the subject utilizing the first device and the second device during a second monitoring period subsequent to the transitionary period, wherein said at least one correlation parameter is applied to signals recorded by at least one of the first device and the second device during the second monitoring period.

In some embodiments, said at least one correlation parameter at least partially compensates for changes in signals recorded by the first device and the second device relative to one another resulting from one or more of differences in locations of the first site and the second site, differences in orientations of the first device and the second device, differences in tissue properties at the first site and the second site, differences in coupling of the first device and the second device at the first site and the second site, respectively, differences in bias pressure in the coupling of the first device and the second device at the first site and the second site, respectively, and differences in electrical and mechanical properties of the first device and the second device.

In some embodiments, said at least one correlation parameter at least partially compensates for changes in signals recorded by the first device and the second device relative to one another resulting from one or more of differences in magnitudes of physiologic signals recorded by the first device and the second device, phase delays between physiologic signals recorded at the first site and the second site, differences in character of the physiologic signals recorded at the first site and the second site, changes in action potentials of the physiologic signals recorded at the first site and the second site, changes in offsets of physiologic signals recorded at the first site and the second site, and changes in frequency spectral content of the physiologic signals recorded at the first site and the second site.

In some embodiments, said at least one correlation parameter comprises at least one of a transfer function and a correction factor.

In some embodiments, generating said at least one correlation parameter comprises correlating changes in one or more of the extracted features of signals recorded by the first device with corresponding extracted features of signals recorded by the second device during at least a portion of the transitionary period, identifying differences in relative changes in the extracted features of signals recorded by the second device with relative changes in the extracted features of signals recorded by the first device for the correlated changes, and generating said at least one correlation parameter for application to signals recorded by at least one of the first device and the second device that offsets at least a portion of the identified differences. The correlated changes may be associated with one or more designated changes in the subject. The one or more designated changes in the subject may comprise changes in one or more of activity level, posture and movement of the subject or an aspect thereof.

In some embodiments, said at least one physiologic parameter comprises an electrocardiogram (ECG) measurement, and generating said at least one correlation parameter comprises extracting wave component features from ECG signals recorded by the first device and the second device, correlating changes in one or more of the wave component features of ECG signals recorded by the first device with corresponding wave component features of ECG signals recorded by the second device during at least a portion of the transitionary period, identifying differences in relative changes in one or more of the wave component features of ECG signals recorded by the second device with relative changes in one or more of the wave component features of ECG signals recorded by the first device for the correlated changes, and generating said at least one correlation parameter for application to ECG signals recorded by at least one of the first device and the second device that offsets at least a portion of the identified differences. The one or more wave component features may comprise one or more of P height, P polarity, Q height, Q polarity, QRS max, ST height, ST polarity, T height, T polarity, baseline noise, baseline wander arrival time, wave shape, relative ratios of waves to one another, beat classification and average ECG construction. Correlating changes in the wave component features of ECG signals obtained by the first device with corresponding wave component features of ECG signals obtained by the second device may be performed on a beat-by-beat basis, or on average ECG signals recorded by the first device and the second device during at least a portion of the transitionary period.

In some embodiments, said at least one correlation parameter comprises a translation component and a rotary component offsetting a location difference between the first site and the second site. The rotary component may represent rotation about a vector normal to a surface of the subject, the rotary component being obtained utilizing one or more orientation sensors and a barometer in the first device and the second device, wherein relative rotational changes are determined by assessing gravitational vectors read by kinematic sensor arrays in the first device and the second device and by measuring barometric height variation between the first device and the second device.

In some embodiments, said at least one physiologic parameter comprises at least one electromyography (EMG) measurement, and generating said at least one correlation parameter comprises extracting action potential features from EMG signals recorded by the first device and the second device, correlating changes in one or more of the action potential features of EMG signals recorded by the first device with corresponding action potential features of EMG signals recorded by the second device during at least a portion of the transitionary period, identifying one or more action potentials visible in EMG signals recorded by the first device and the second device during said portion of the transitionary period, determining relative changes in amplitude of the one or more action potentials visible in EMG signals recorded by the first device and the second device during said portion of the transitionary period, and generating said at least one correlation parameter by generating one or more correction factors that adjust the amplitude of the one or more action potentials recorded by the second device so as to estimate an amplitude of action potentials that would be recorded by the first device.

In some embodiments, said at least one physiologic parameter comprises a core temperature measurement, and generating said at least one correlation parameter comprises extracting, from one or more sensors of each of the first device and the second device, a corresponding thermal gradient measured based on comparisons of sensor readings from a first subset of the sensors oriented to make thermal contact with the subject with sensor readings from a second subset of the sensors oriented to make thermal contact with ambient surroundings of the first and second devices, estimating core temperature readings of the subject based on temperature readings from the first subset of sensors of the first and second devices and the corresponding thermal gradients, correlating changes in core temperature readings from the first device and the second device during at least a portion of the transitionary period, and generating said at least one correlation parameter by combining the correlated changes in core temperature readings of the subject from the first device and the second device. The method may further include determining which of the first device and the second device has a lowest thermal gradient and weighting said at least one correlation parameter to the device having the lowest thermal gradient. In some embodiments, the first site is associated with a lower thermal gradient than the second site, with the second site being more conducive to long-term wear relative to the first site.

In some embodiments, said at least one physiologic parameter comprises a bioimpedance measurement, and generating said at least one correlation parameter comprises extracting local measures of water content from bioimpedance signals recorded by the first device and the second device, correlating changes in the local measures of water content recorded by the first device with corresponding local measures of water content recorded by the second device during at least a portion of the transitionary period, identifying differences in relative changes in the local measures of water content recorded by the second device with relative changes in the local measures of water content recorded by the first device for the correlated changes, and generating said at least one correlation parameter for application to bioimpedance signals recorded by at least one of the first device and the second device that offsets at least a portion of the identified differences. The correlated changes in the local measures of water content may be associated with a series of postural changes by the subject.

In some embodiments, an apparatus comprises a memory and a processor coupled to the memory, with the processor being configured to perform one or more aspects of the above-described methods.

In some embodiments, a non-transitory processor-readable storage medium has stored therein program code of one or more software programs, wherein the program code when executed by at least one processing device causes said at least one processing device to perform one or more aspects of the above-described methods.

In one embodiment, an apparatus comprises a memory and a processor coupled to the memory and configured to coordinate data collection and recharging of two or more monitoring devices by indicating to a user a location of a first monitoring site and a time at which a first one of the monitoring devices is to be attached to a subject at the first monitoring site for a first monitoring period and at which one or more other ones of the monitoring devices are to be attached to a charging station, indicating to the user a time at which the first monitoring period ends and a second one of the monitoring devices is to be attached to the subject at a second monitoring site for a transitionary monitoring period, and indicating to a user a time at which the transitionary monitoring period ends and one of the first monitoring device and the second monitoring device is to be removed from the subject and attached to the charging station.

In some embodiments, the second monitoring device is attached to the charging station prior to the end of the first monitoring period.

In some embodiments, the processor is further configured to obtain monitoring data recorded by the first monitoring device and the second monitoring device, the monitoring data comprising one or more signals associated with at least one physiological parameter of the subject, to extract, from the monitored data, one or more features of signals recorded by the first monitoring device and the second monitoring device during the transitionary period when the first monitoring device and the second monitoring device are simultaneously monitoring said at least one physiological parameter of the subject, to generate at least one correlation parameter by analyzing the extracted features of the signals recorded by the first monitoring device and the second monitoring device for at least a portion of the transitionary period, said at least one correlation parameter when applied to signals recorded by at least one of the first monitoring device and the second monitoring device at least partially compensating for changes in signals recorded by the first monitoring device and the second monitoring device relative to one another, and to apply said at least one correlation parameter to signals recorded by at least one of the first monitoring device and the second monitoring device.

In some embodiments, a monitoring kit comprises the above-described apparatus, the charging station and the two or more monitoring devices. The above-described apparatus may be implemented within at least one of the two or more monitoring devices, within the charging station, or in a processing device separate from the charging station and the two or more monitoring devices. The processing device may comprise a server, or a mobile device such as a tablet, smartphone, smartwatch, laptop, etc.

In one embodiment, a method for monitoring a subject comprises attaching a first device to the subject at a first site, monitoring said at least one physiological parameter of the subject utilizing the first device for a first monitoring period, attaching a second device to the subject at a second site, monitoring said at least one physiological parameter of the subject utilizing the first device and the second device during a transitionary period, removing the first device from the subject following the transitionary period, and monitoring said at least one physiological parameter of the subject utilizing the second device during a second monitoring period subsequent to the transitionary period.

In some embodiments, the method further comprises analyzing signals recorded by the first device and the second device during the transitionary period to generate at least one correlation parameter, said at least one correlation parameter when applied to signals recorded by at least one of the first device and the second device at least partially offsetting differences in the signals recorded by the first device and the second device relative to one another.

BRIEF DESCRIPTION OF THE DRAWINGS

Several aspects of the disclosure can be better understood with reference to the following drawings. In the drawings, like reference numerals designate corresponding parts throughout the several views.

FIGS. 2A-2C illustrate device replacement, according to an embodiment of the invention.

FIGS. 4A-4D illustrate another patch replacement, according to an embodiment of the invention.

FIGS. 9A and 9B show plots of signals obtained from first and second devices, according to an embodiment of the invention.

DETAILED DESCRIPTION

Figure 1A:
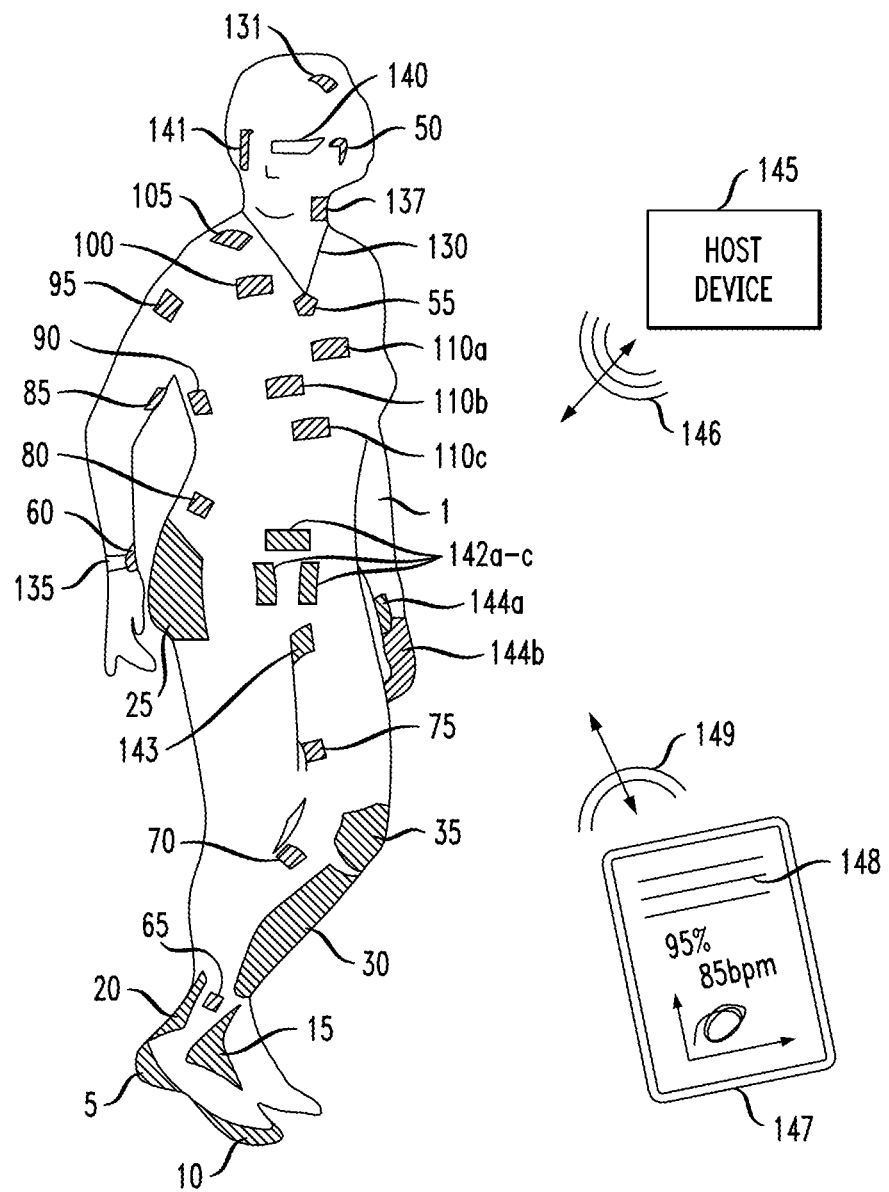
FIGS. 1A-1D illustrate aspects of a modular physiologic monitoring system, according to an embodiment of the invention.

Particular embodiments of the present disclosure are described herein below with reference to the accompanying drawings; however, the disclosed embodiments are merely examples of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures A modular physiologic monitoring system in accordance with the present disclosure for assessing one or more physiologic parameters of a subject (e.g., a human subject, a patient, an athlete, a trainer, an animal, such as equine, canine, porcine, bovine, etc.) with a body may include one or more patches, each patch adapted for attachment to the body of the subject (e.g., attachable to the skin thereof, reversibly attachable, adhesively attachable, with a disposable interface and a reusable module, etc.). In aspects, the physiologic monitoring system may include one or more modules, each module may include a power source (e.g., a battery, a rechargeable battery, an energy harvesting transducer, microcircuit, and an energy reservoir, a thermal gradient harvesting transducer, a kinetic energy harvesting transducer, a radio frequency energy harvesting transducer, a fuel cell, a biofuel cell, etc.), signal conditioning circuitry, communication circuitry, one or more sensors, or the like, configured to generate one or more signals (i.e., physiologic and/or physical signals).

One or more of the patches may include one or more interconnects, configured and dimensioned so as to couple with one or more of the modules, said modules including a complimentary interconnect configured and dimensioned to couple with the corresponding patch. The patch may include a bioadhesive interface for attachment to the subject, the module retainable against the subject via interconnection with the patch.

In aspects, the patch may be configured so as to be single use (i.e., disposable). The patch may include a thin, breathable, stretchable laminate. In aspects, the laminate may include a substrate, a bioadhesive, one or more sensing elements in accordance with the present disclosure, and one or more interconnects for coupling one or more of the sensing elements with a corresponding module.

In aspects, to retain a high degree of comfort and long term wear-ability of the patch on a subject, to limit interference with normal body function, to limit interference with joint movement, or the like, the patch may be sufficiently thin and frail, such that it may not substantially retain a predetermined shape while free standing. Such a definition is described in further detail below. The patch may be provided with a temporary stiffening film to retain the shape thereof prior to placement of the patch onto the body of a subject. Once adhered to the subject, the temporary stiffening film may be removed from the patch. While the patch is adhered to the subject, the shape and functionality of the patch may be substantially retained. Upon removal of the patch from the subject, the, now freestanding patch is sufficiently frail such that the patch can no-longer substantially retain the predetermined shape (i.e., sufficiently frail such that the patch will not survive in a free standing state). In aspects, stretch applied to the patch while removing the patch from the subject may result in snap back once the patch is in a freestanding state that renders such a patch to crumple into a ball and no longer function.

In aspects, the patch may include a film (e.g., a substrate), with sufficiently high tear strength, such that, as the patch is peeled from the skin of a subject, the patch does not tear. In aspects, the ratio between the tear strength of the patch and the peel adhesion strength of the patch to skin (i.e., tear strength:peel adhesion strength), is greater than 8:1, greater than 4:1, greater than 2:1, or the like. Such a configuration may be advantageous so as to ensure the patch may be easily and reliably removed from the subject after use without tearing.

In aspects, the patch may include a bioadhesive with peel tack to mammalian skin of greater than 0.02 N/mm, greater than 0.1 N/mm, greater than 0.25 N/mm, greater than 0.50 N/mm, greater than 0.75 N/mm, or the like. Such peel tack may be approximately determined using an American Society for Testing and Materials (ASTM) standard test, ASTM D3330: Standard test method for peel adhesion of pressure-sensitive tape.

In aspects, the patch may exhibit a tear strength of greater than 0.5 N/mm, greater than 1 N/mm, greater than 2 N/mm, greater than 8 N/mm, or the like. Such tear strength may be approximately determined using an ASTM standard test, ASTM D624: Standard test method for tear strength of conventional vulcanized rubber and thermoplastic elastomers.

In aspects, the patch may be provided with a characteristic thickness, of less than 50 micrometer (μm), less than 25 μm, less than 12 μm, less than 8 μm, less than 4 μm, or the like. Yet, in aspects, a balance between the thickness, stiffness, and tear strength may be obtained so as to maintain sufficiently high comfort levels for a subject, minimizing skin stresses during use (i.e., minimizing skin stretch related discomfort and extraneous signals as the body moves locally around the patch during use), minimizing impact on skin health, minimizing risk of rucking during use, and minimizing risk of maceration to the skin of a subject, while limiting risk of tearing of the patch during removal from a subject, etc.

In aspects, the properties of the patch may be further altered so as to balance the hydration levels of one or more hydrophilic or amphiphilic components of the patch while attached to a subject. Such adjustment may be advantageous to prevent over hydration or drying of an ionically conducting component of the patch, to manage heat transfer coefficients within one or more elements of the patch, to manage salt retention into a reservoir in accordance with the present disclosure, and/or migration during exercise, to prevent pooling of exudates, sweat, or the like into a fluid measuring sensor incorporated into the patch or associated module, etc. In aspects, the patch or a rate determining component thereof may be configured with a moisture vapor transmission rate of between 200 $g/m^2/24$ hrs and 20,000 $g/m^2/24$ hrs, between 500 $g/m^2/24$ hrs and 12,000 $g/m^2/24$ hrs, between 2,000 $g/m^2/24$ hrs and 8,000 $g/m^2/24$ hrs, or the like.

Such a configuration may be advantageous for providing a comfortable wearable physiologic monitor for a subject, while reducing material waste and/or cost of goods, preventing contamination or disease spread through uncontrolled re-use, and the like.

In aspects, one or more patches and/or modules may be configured for electrically conducting interconnection, inductively coupled interconnection, capacitively coupled interconnection, with each other. In the case of an electrically conducting interconnect, each patch and module interconnect may include complimentary electrically conducting connectors, configured and dimensioned so as to mate together upon attachment. In the case of an inductively or capacitively coupled interconnect, the patch and module may include complimentary coils or electrodes configured and dimensioned so as to mate together upon attachment.

Each patch or patch/module pair may be configured to monitor one or more local physiologic and/or physical parameters of the attached subject (e.g., local to the site of attachment, etc.), local environment, combinations thereof, or the like, and to relay such information in the form of signals to a host device (e.g., via a wireless connection, via a body area network connection, or the like), one or more patches or modules on the subject, or the like.

In aspects, the host device may be configured to coordinate information exchange to/from each module and/or patch, and to generate one or more physiologic signals, physical signals, environmental signals, kinetic signals, diagnostic signals, alerts, reports, recommendation signals, commands, combinations thereof, or the like for the subject, a user, a network, an electronic health record (EHR), a database (e.g., as part of a data management center, an EHR, a social network, etc.), a processor, combinations thereof, or the like.

In aspects, a system in accordance with the present disclosure may include a plurality of substantially similar modules (i.e., generally interchangeable modules, but with unique identifiers), for coupling with a plurality of patches, each patch, optionally different from the other patches in the system (e.g., potentially including alternative sensors, sensor types, sensor configurations, electrodes, electrode configurations, etc.). Each patch may include an interconnect suitable for attachment to an associated module. Upon attachment of a module to a corresponding patch, the module may validate the type and operation of the patch to which it has been mated. In aspects, the module may then initiate monitoring operations on the subject via the attached patch, communicate with one or more patches on the subject, a hub, etc. The data collection from each module may be coordinated through one or more modules and/or with a host device in accordance with the present disclosure. The modules may report a time stamp along with the data in order to synchronize data collection across multiple patch/module pairs on the subject, between subjects, etc. Thus, if a module is to be replaced, a hot-swappable replacement (i.e., replacement during a monitoring procedure) can be carried out easily by the subject, a caregiver, practitioner, etc. during the monitoring process. Such a configuration may be advantageous for performing redundant, continuous monitoring of a subject, and/or to obtain spatially relevant information from a plurality of locations on the subject during use.

In aspects, the modules and/or patches may include corresponding interconnects for coupling with each other during use. The interconnects may include one or more connectors, configured such that the modules and patches may only couple in a single unique orientation with respect to each other. In aspects, the modules may be color coded by function. A temporary stiffening element attached to a patch may include instructions, corresponding color coding, etc. so as to assist a user or subject with simplifying the process of monitoring.

FIGS. 1A-1D show aspects of modular physiologic monitoring systems in accordance with the present disclosure.

FIG. 1A shows a subject 1 with a series of patches and/or patch/module pairs each in accordance with the present disclosure attached to the subject 1 at sites described below, a host device 145 in accordance with the present disclosure, a feedback/user device 147 in accordance with the present disclosure displaying some data 148 based upon signals obtained from the subject 1, and one or more feedback devices 135, 140, in accordance with the present disclosure configured to convey to the subject 1 one or more aspects of the signals or information gleaned therefrom. The host device 145, the user device 147, the patches and/or patch module pairs, and/or the feedback devices 135, 140 may be configured for wireless communication 146, 149 during a monitoring session.

In aspects, a patch/module pair may be adapted for placement almost anywhere on the body of a subject 1. As shown in FIG. 1A, some sites may include attachment to the cranium or forehead 131, the temple, the ear or behind the ear 50, the neck, the front, side, or back of the neck 137, a shoulder 105, a chest region with minimal muscle mass 100, integrated into a piece of ornamental jewelry 55 (may be a host, a hub, a feedback device, etc.), arrangement on the torso 110a-c, arrangement on the abdomen 80 for monitoring movement or breathing, below the rib cage 90 for monitoring respiration (generally on the right side of the body to substantially reduce EKG influences on the measurements), on a muscle such as a bicep 85, on a wrist 135 or in combination with a wearable computing device 60 on the wrist (e.g., a smart watch, a fitness band, etc.), on a buttocks 25, on a thigh 75, on a calf muscle 70, on a knee 35 particularly for proprioception based studies and impact studies, on a shin 30 primarily for impact studies, on an ankle 65, over an Achilles tendon 20, on the front or top of the foot 15, on a heel 5, or around the bottom of a foot or toes 10. Other sites for placement of such devices are envisioned. Selection of the monitoring sites is generally determined based upon the intended application of the patch/module pairs described herein.

Additional placement sites on the abdomen, perineal region 142a-c, genitals, urogenital triangle, anal triangle, sacral region, inner thigh 143, or the like may be advantageous in the assessment of autonomic neural function of a subject. Such placements regions may be advantageous for assessment of PNS activity, somatosensory function, assessment of SNS functionality, etc.

Placement sites on the wrist 144a, hand 144b or the like may advantageous for interacting with a subject, such as via performing a stress test, performing a thermal stress test, performing a tactile stress test, monitoring outflow, afferent traffic, efferent traffic, etc.

Placement sites on the nipples, areola, lips, labia, clitoris, penis, the anal sphincter, levator ani muscle, over the ischiocavernous muscle, deep transverse perineal muscle, labium minus, labium majus, one or more nerves near the surface thereof, posterior scrotal nerves, perineal membrane, perineal nerves, superficial transverse perineal nerves, dorsal nerves, inferior rectal nerves, etc. Such placement may be advantageous for assessment of autonomic neural ablation procedures, autonomic neural modulation procedures, assessment of the PNS of a subject, assessment of sexual dysfunction of a subject, etc.

Placement sites on the face 141, over ocular muscles, near the eye, over a facial muscle (e.g., a nasalis, temporalis, zygomaticus minor/major, orbicularis oculi, occipitofrontalis), near a nasal canal, over a facial bone (e.g., frontal process, zygomatic bone/surface, zygomaticofacial foreman, malar bone, nasal bone, frontal bone, maxilla, temporal bone, occipital bone, etc.), may be advantageous to assess ocular function, salivary function, sinus function, interaction with the lips, interaction with one or more nerves of the PNS (e.g., interacting with the vagus nerve within, on, and/or near the ear of the subject), etc.

In aspects, a system in accordance with the present disclosure may be configured to monitor one or more physiologic parameters of the subject 1 before, during, and/or after one or more of, a stress test, consumption of a medication, exercise, a rehabilitation session, a massage, driving, a movie, an amusement park ride, sleep, intercourse, a surgical, interventional, or non-invasive procedure, a neural remodeling procedure, a denervation procedure, a sympathectomy, a neural ablation, a peripheral nerve ablation, a radio-surgical procedure, an interventional procedure, a cardiac repair, administration of an analgesic, a combination thereof, or the like. In aspects, a system in accordance with the present disclosure may be configured to monitor one or more aspects of an autonomic neural response to a procedure, confirm completion of the procedure, select candidates for a procedure, follow up on a subject after having received procedure, assess the durability of a procedure, or the like (e.g., such as wherein the procedure is a renal denervation procedure, a carotid body denervation procedure, a hepatic artery denervation procedure, a LUTs treatment, a bladder denervation procedure, a urethral treatment, a prostate ablation, a prostate nerve denervation procedure, a cancer treatment, a pain block, a neural block, a bronchial denervation procedure, a carotid sinus neuromodulation procedure, implantation of a neuromodulation device, tuning of a neuromodulation device, etc.).

Figure 1B:
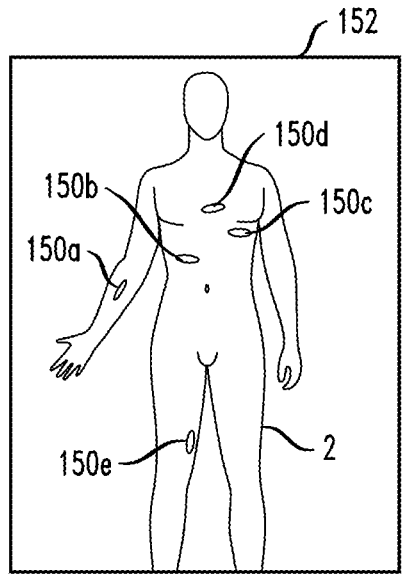

FIG. 1B shows a series of patch/module pairs 150a-e each in accordance with the present disclosure placed upon a subject 2 as part of a monitoring session in accordance with the present disclosure, in this case an EKG monitoring session. An image 152 of the subject 2 has been taken and may be analyzed in accordance with the present disclosure to calculate one or more standard lead configurations from the arrangement of patch/modules 150a-e shown.

Figure 1C:
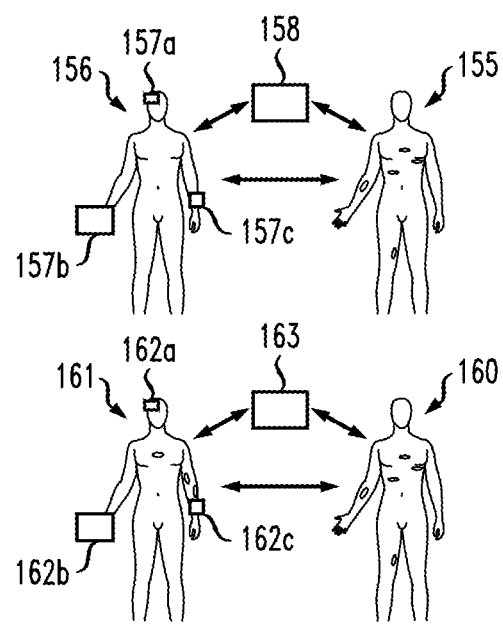

FIG. 1C shows aspects of communication between subjects 155, 160 and non-subject users 156, 161 partaking in a monitoring session in accordance with the present disclosure. In a first aspect, the subject 155 is wearing a series of patches and modules each in accordance with the present disclosure configured to communicate with one or more of a host device 158, a display 157b, a HUD, a pair of virtual reality goggles, a Google Glasses™ based feedback device 157a (i.e., potentially via a smartphone hub), and/or a wristwatch 157c to communicate one or more feedback signals in accordance with the present disclosure to the user 156.

In aspects, the subject 160 may wear a series of patches and modules each in accordance with the present disclosure configured to communicate with one or more of a host device 163, a display 162b, a virtual reality headset, a HUD, a Google Glasses™ based feedback device 162a (i.e., via a smartphone hub), a wristwatch 162c, and/or one or more patches and/or modules configured upon the body of the user 161 to communicate one or more feedback signals in accordance with the present disclosure to the user 161 or to convey one or more sensations to the body of the user 161 (i.e., via the attached patches). In aspects, the ocular feedback device 162a, may be used to perform a visual and/or audible stress test on the subject, one or more aspects of the feedback device 162a, or an associated patch configured to monitor the response of one or more aspects of the ANS to the stress test.

In aspects, the communication between the subjects 155, 160 and the users 156, 161 may be bidirectional (i.e., the subject 155, 160 may also receive information corresponding to physiologic and/or physical information obtained from the user 156, 161).

Figure 1D:
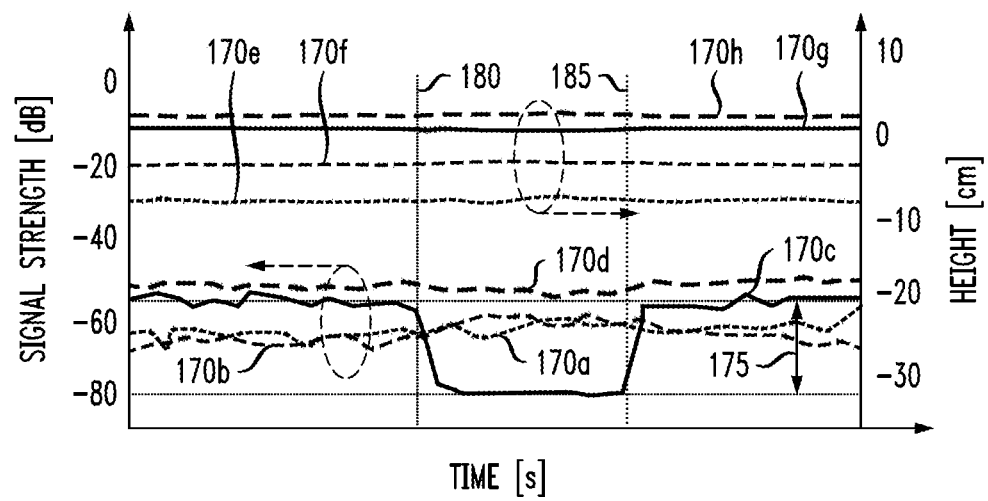

FIG. 1D shows a time series example of an identification process for a patch/module pair in accordance with the present disclosure. In the non-limiting example shown, the modules are equipped with radios, each radio capable of sending a signal with a predetermined signal strength (left vertical axis) and equipped with a barometer or altimeter calibrated to give a relative height signal (right vertical axis). In aspects, a user, a program on a feedback device, on a host device, on a user device, etc. may prompt a subject or user to cover a particular patch on the body of the subject (e.g., communicated to the subject or user via an instruction pamphlet, via a screen prompt, etc.). When the prompted module is covered (period between timestamps 180, 185) the signal strength of the module is changed by a substantially identifiable amount 175. Thus a simple procedure may be used to identify a module in the BAN, correlate a module on a particular site on the subject with a corresponding ID received by the host device, etc. Other aspects and variants of a localization and/or orientation procedure are discussed throughout this disclosure.

Additional details regarding modular physiologic monitoring systems, kits and methods are further described in PCT application serial no. PCT/US2014/041339, published as WO 2014/197822 and titled "Modular Physiologic Monitoring Systems, Kits, and Methods," and PCT application serial no. PCT/US2015/043123, published as WO 2016/019250 and titled "Modular Physiologic Monitoring Systems, Kits, and Methods, the disclosures of which are incorporated by reference herein in their entirety.

Described below are various embodiments facilitating long-term continuous monitoring of a subject, such as for use in the above-described modular physiologic monitoring system. It is to be appreciated, however, that embodiments are not limited to the specific modular physiologic monitoring system shown and described with respect to FIGS. 1A-1D, or with respect to the particular patch-module pairs previously described. Instead, embodiments are more broadly applicable to devices for which it is desired to provide signal continuity or calibration in a long-term monitoring scenario. In this context, "long-term" refers to a monitoring session which exceeds the usable life of a device.

Consider a device comprising a patch-module pair as described herein. In some cases, the module in the patch-module pair may be considered the life-determining component of the device. For example, the module may have a battery life that is less than the time period of a monitoring session, thus necessitating replacement during the monitoring session. In other cases, the patch in the patch-module pair may be considered the life-determining component of the device. For example, the patch, a bioadhesive on the patch, one or more electrodes or other sensors on the patch, or the like may become degraded over time during a monitoring process thus necessitating replacement during the monitoring session. In some embodiments, it may be advantageous to limit the life of any one patch attachment to maintain good skin health. The life of a patch attachment, for example, may be limited to less than 5 days, less than 3 days, less than 2 days, or the like. In the course of a long-term monitoring session, it may be possible that both a patch and a module are to be replaced, either at the same time or asynchronously. A device used in a long-term monitoring session may also be physically frail or degradable, such that the device or a component thereof is expected to fail or become unusable for monitoring at some point during a monitoring session, thus necessitating device replacement.

It is also important to note that although various embodiments are described herein in the context of device replacement, such as replacing a module and/or patch, embodiments are not limited solely to replacement of devices. As described in further detail below, in some embodiments continuous long-term monitoring may be facilitated by synchronization or other coordination of multiple devices attached to a subject, possibly in sequence. For example, two or more devices may be attached to a subject to provide monitoring at different locations or sites on the subject, to provide redundancy in the monitoring at a particular site on a subject, etc.

As described above, patches and/or modules in a modular physiologic monitoring system may be replaced over time so as to provide continuous monitoring of a subject. For example, modules may be powered by an internal energy source such as a battery. In some cases, monitoring of a subject may extend for a time period longer than the battery life of a module. In such cases, it may be desired to provide a replacement module to facilitate redundant and/or continuous monitoring of a subject over the monitoring period. In other cases, it may be desired to replace a module during a monitoring period for various other reasons in addition to or in place of replacing a module to recharge its battery or other energy source. Such reasons include but are not limited to troubleshooting or performing diagnostics on a module, upgrading or replacing existing modules with newer modules, reading data stored on a module during the monitoring session, etc.

In some embodiments, it may also be desired to provide for replacement of patches that the above-described modules mate or otherwise interconnect with. For example, over time a patch or other subject interface may become worn out, degraded or otherwise need replacement (such as to upgrade to a newer type of patch, etc.). In such cases, a module may be moved or swapped from an "old" patch that is to be replaced with a "new" patch. It is to be appreciated that the terms "old" and "new" in this context do not necessarily refer to the age of a patch. Patches or other interfaces between a module and a subject may be reusable, and thus a module in some cases may be moved from an older-aged patch to a younger-aged patch or vice-versa.

In one approach for facilitating an extended monitoring period, devices such as modules and/or patches may be sized or designed to have characteristics facilitating use over the extended monitoring period. As an example, a module may be sized with a battery having capacity or battery life that exceeds the expected wear time of the module (e.g., with battery life that matches or exceeds a length of the extended monitoring period). As another example, the memory capacity of the module may be chosen to exceed an amount of data to be collected over the expected wear time of the module (e.g., with memory sufficient to store monitoring data collected over a period of time that matches or exceeds the length of the extended monitoring period). As a further example, a subject interface such as a patch may be designed for extended wear time, or a longest possible wear time (e.g., for adhesive wear time matching or exceeding the length of the extended monitoring period). Designing devices such as modules and patches to meet such specifications for extended monitoring periods, however, leads to various drawbacks. Such drawbacks include: that the resulting battery size generally dictates the overall size of the wearable device; that memory size can be a key component related to system cost; and that the choice of long-term single use adhesive interface dictates the aggressiveness or comfort of the wearable device. Thus, such specifications or criteria can result in very cumbersome, expensive, and uncomfortable devices. Further, detaching the device from the subject during use (e.g., typically in an unintended matter, although possibly intentional by the user due to discomfort) can mean loss of data and resulting failure of the extended monitoring period on the whole.

The above-described disadvantages may be overcome in some embodiments utilizing hot-swapping approaches described herein, which allow for an alternate device and subject interface design methodology. For example, characteristics such as battery life, memory and wear time do not have to be designed for a "worst case" scenario (e.g., to match or exceed the length of the extended monitoring period). Instead, such characteristics may be designed or established for more reasonable wear periods (e.g., such as greater than 12 hours, greater than 1 day, greater than 2 days, less than 2 days, less than 3 days, less than 4 days, etc.) to reduce the size and cost of devices as well as increase comfort and wearability for the subject or user. It is important to note that wear periods for devices such as modules and patches described herein may be variable, and dependent on various factors including but not limited to wear conditions, subject skin, sweating, and the like. Further, different devices which are hot-swapped for one another may be configured for different wear times (e.g., a module may be hot-swapped for another module with a different battery life, memory, subject interface, etc.).

Hot-swapping approaches described herein allow for extending the wear time beyond an "intermediate" monitoring period (e.g., a wear period for one device) that is less than a length of the extended monitoring period by hot-swapping from one device to a next maintaining continuous monitoring of the subject. The intermediate monitoring period can thus be extended indefinitely as required for a particular usage scenario by performing multiple hot-swaps between devices. This allows for optimized sizing and design of the devices, such as battery and memory features, while supporting flexible wear time for the subject interface.

Devices attached to a subject can be monitored during use to determine when the devices should be swapped, or when an intermediate monitoring period should end. This may be in response to detecting various conditions, including: detecting a battery drained condition corresponding to low battery life according to some designated threshold; a memory full condition corresponding to when available memory or storage is low according to some designated threshold; on determining that the subject interface is changing or deteriorating over the intended wear time; on detecting deleterious sensor readings or other sensor errors; on detecting degradation or other failure or potential failure of a device or one or more components thereof; and/or the like. Such criteria can be used to generate notifications or other indications to another device, such as a computing or processing device associated with a user, a subject, a caregiver, etc. to change the device (e.g., a module or patch) with another utilizing the hot-swap procedures described herein. The user, subject or caregiver may be prompted or notified when one or more wear time limits or thresholds are met, so as to initiate hot-swapping.

Hot-swapping approaches described herein thus provide significant advantages, in allowing for the use of monitoring devices such as modules and patches with limited size, profile, cost, weight, etc. Limiting the wear time of devices can further provide more hygienic monitoring conditions, as subject interfaces can be replaced and refreshed more often.

Provided herein are methods for maintaining signal continuity and calibration among multiple devices during continuous long-term monitoring. For example, in applications where the period of monitoring exceeds the life cycle of a single patch, one must remove an old patch and apply a new one to continue monitoring. In using patches with low cost of goods (COGs) and simple patch-to-hub or patch-to-module interconnects, it may be advantageous to attach a "next" patch before removing a "previous" patch. While the "next" and "previous" patch (or similarly "next" and "previous" modules, or more generally "next" and "previous" devices) are attached to a subject, there may be a period of simultaneous monitoring. Information obtained during the period of simultaneous monitoring can be used to maintain signal continuity, to determine relative positioning between the new and old patches, to calibrate signals from the new patch with or against signals from the old patch, etc. before the old patch is removed and monitoring continues with the new patch. As mentioned above, in some embodiments the old patch is not removed, such as in cases where the new patch provides redundancy for the old patch, for monitoring using multiple patches or devices, etc.

In some embodiments, it may be advantageous to monitor one or more physiologic parameters (e.g., ECG, EMG, skin temperature, proprioceptive signals, etc.) from a plurality of sites on a subject so as to perform a redundant and/or higher order assessment of that physiologic function.

In terms of redundancy, in a life-critical ECG monitoring application, it may be critical to maintain the robust recording of an ECG under a wide range of usage scenarios. A plurality of monitoring devices placed on the subject may allow for soft failure of the monitoring at some subset of the monitoring devices to occur without adversely impacting continuous monitoring of the subject. Soft failure may refer to instances wherein one or more of the devices or device interfaces fail to capture a reliable signal from the subject, run low on battery, cannot transmit signal to an off-subject host, etc. In cases of soft failure, other redundant devices allow for continued and uninterrupted monitoring of the subject.

In terms of higher order assessment of a physiologic function, the collective monitoring of one or more physiologic functions from a subject at a plurality of sites may be advantageous for providing further diagnostic information from the monitoring session. In one non-limiting example, a plurality of devices may be applied to a subject and simultaneous ECG signals obtained from each one. Dependent upon the locations on the subject to which the devices are applied, the ECG obtained by each device may provide a distinct vantage point for observing the 3D field generated by the heart during operation. Collectively the simultaneous readings from several locations in the 3D field, which may be collected by unconnected devices on the subject, may be combined so as to generate a vector ECG of the subject. With additional information about the actual positions of the individual devices and orientations thereof, a 3, 5, or 12-lead ECG equivalent from the subject may be obtained through the collective monitoring from the plurality of devices in association with algorithmic adjustment to correct for specific positional relationships of the devices on the subject during the specific monitoring session. Such higher level diagnostic information may provide more information about the region of the heart with a disorder as is known in the art.

To maintain device performance during chronic or long-term monitoring, it is desired to provide functionality allowing for coordination or synchronization between multiple devices attached to a subject.

Described herein are methods for such coordination of multiple devices attached to a subject, as well as systems and devices used in performing such methods for coordination of multiple devices. For example, a system may provide wireless networks or interfaces supporting simultaneous recording from multiple devices. Devices to be coordinated or synchronized may include sensors that assist in coordinating the location of such devices on a subject with respect to one another. In some embodiments, the sensors may be secondary or dedicated sensors provided solely for such location coordination. In other embodiments, existing sensors of a device may be specially programmed or configured via a processor of the device to provide such location coordination functionality. The device, in addition to location coordination functionality, may also be programmed or configured (possibly in conjunction with a separate processor) with various other functionality.

In some embodiments, devices may be programmed with functionality for maintaining continuity between measured signals, such as physiological parameters of a subject. For example, algorithms are provided for comparing data streams from multiple devices, which may be used for applying a correction factor. Information obtained using the location coordination functionality may be used in generating the correction factor.

Devices may be programmed with functionality improving bioimpedance monitoring in some embodiments. Simultaneous monitoring with multiple devices allows for viewing of not only offset related changes caused by a new contact site but also changes in impedance during postural changes, movement of a subject, etc. as recorded simultaneously at multiple contact sites. This information may be used to rationalize the variance seen between two or more devices or recording sites, and to compensate for such variance in recording after transitioning to a new device so as to maintain consistency of the recording over time.

In other embodiments, devices may be programmed with functionality for reducing artifacts during monitoring. Artifacts may enter into monitoring in several ways. In some cases, artifacts may be due to differences in monitoring sites, due to device-specific differences, due to movement, other physiologic processes, local muscle activity, contact of the device with the surroundings, electromagnetic interference, etc. Monitoring site-specific issues include, by way of example, different tissue hydration or other dermis properties between sites, varying dermis properties over time, contact or other device-subject interface variations, etc. Device-specific issues include differences in electrode impedance, component impedance variation, quality of tissue contact, history of stretch applied at the monitoring site over the monitoring period, etc. By simultaneously monitoring both sites for a period of time, it is possible to see how recordings from both sites change when recording essentially the same physiologic parameter of the subject, and thus differences in the data can be corrected to maintain correlation (as close as possible) between data from multiple devices.

Coordination of multiple devices may include hot-swapping devices. Hot-swapping may include single-device and multiple-device arrangements.

In multiple-device arrangements, one device is placed on a charger or is otherwise made ready or available for swapping with a device attached or applied to a subject. Consider, as an example, an embodiment wherein the device is a patch/module pair. A first patch is attached to the subject, and a first module is attached to the first patch while a second module is attached to a charger or otherwise made available for attachment to the subject. When it is time to change the first patch out, a second patch is applied to the subject. The second patch may optionally be attached near to the first patch, such as within a threshold distance of the first patch, a threshold distance of a desired monitoring site, or both. The second hub, which is attached to the charger or otherwise made available for attachment to the subject, is then placed on the second patch.

For a transitionary period, both the first module and the second module are attached to the subject, via the respective first and second patches, and monitor the subject. After the transitionary period, the first patch and first module are removed. The first module may be placed on the charger or otherwise made available for subsequent attachment to the subject (e.g., in the event that the second patch is to be replaced with a third patch). The second module stays attached to the second patch and continues to collect data from the subject.

In some embodiments, monitoring sites are specific. For example, if monitoring a bicep EMG, a first device may be attached to a subject and calibrated while the subject works out that muscle group. When the second device is attached to the subject, it may not be permitted to overlap with the first device due to physical constraints, and thus it is at least some distance away from the attachment site of the first device. Due to such location differences, there may be a transfer function between the electromyograms obtained from the first and second sites, including a contribution by fibers captured by the first and second devices. There may be a subset of action potentials that are seen by both devices, and other subsets of action potentials seen primarily by only one of the devices. By simultaneously monitoring with both devices while the subject uses the muscle group, it is possible to identify which action potentials belong to the subset seen by both devices, and to then correlate the amplitudes of such action potentials to estimate a new transfer function allowing for continuous calibrated monitoring of activity and exertion level of the target muscle group without having to recalibrate the second device.

The threshold distances between attachment sites of first and second devices as well as the threshold distances between a given device and a desired monitoring site, may vary based on application. For example, some types of monitoring may have more flexibility in the threshold distances, while others may benefit from more precision and thus lower threshold distances. In some cases, the threshold distance may be based on or determined from the size of the muscle groups being targeted with respect to the electrode and/or device sizes, as well as how readily first and second device electrodes can be oriented so as to engage a target region. In some embodiments, threshold distances may be less than 50 mm, less than 25 mm, less than 10 mm, or the like. It is also important to note that orientation of devices may also differ, which may affect monitoring. For example, when monitoring EMG the muscle groups being targeted may not be that large, such that getting a second device close to the first device may be difficult without changing the orientation of the device. In some embodiments, one or more electrodes may be positioned near to the target muscle and one or more electrodes on each device may act as a reference or counter electrode, positioned so as to be away from the target muscle. In aspects, a multi-patch and/or multi-electrode configuration may be used to determine the activity associated with a target muscle group, even when simultaneously monitoring the activity of other groups (either on purpose, or due to placement issues, placement proximity challenges, etc.). As will be discussed below, synchronization between devices may account for such variance in orientation.

In single-device arrangements, one module may be moved from one patch to another. A first patch may be attached to the subject, where the single module is attached to the first patch. When the first patch is to be replaced, the single module can buffer data during a transitionary period. The buffered data may be stored on the module itself or on a host device separate from the module, such as a monitoring system described below. In some embodiments, the first and second patches may have built-in memory. In these embodiments, buffered data may be stored on the first or second patch. Patches, however, may be designed to be low cost and easily replaceable, and configuring low cost patches to include built-in memory may be cost-prohibitive in certain applications. After buffering data, the single module can then be transferred to a second patch, with the buffered data being used to recalibrate physiological parameters of the subject for the patch position, electrical properties, etc. of the second patch. The first patch can then be removed with monitoring continuing using the module attached to the second patch.

As a general matter, multiple-device arrangements may provide significant benefits relative to single-device arrangements as simultaneous monitoring from two or more devices is useful in constructing accurate change-over parameters to move recording from a first site to a second site. In certain situations, such as when only a single module is available, single-device arrangements may be useful.

In single-device arrangements, the single module may have a "switch mode" to facilitate seamless or near seamless syncing between the first patch and the second patch. In responsive to activating the switch mode, the single module can begin storing data from the first patch, which is then written to a buffer. After switching or moving the single module to the second patch, the buffered data is used to facilitate the seamless syncing in a special swap mode with minimal interaction required from a user.

The single-device and multiple-device arrangements described herein can provide a number of advantages, such as in facilitating the in-place calibration of bioimpedance, tissue strain, temperature, electrocardiogram (ECG) positioning (e.g., such as to determine relative placement positions of a new patch with respect to an old patch), electromyography (EMG) calibration, maintaining a continuous signal throughout a monitoring session, etc.

Various example use case scenarios will now be described with respect to FIGS. 2A-2C, 3A-3E, 4A-4D and 5A-5C. FIGS. 2A-2C illustrate device replacement, FIGS. 3A-3E illustrate patch replacement using multiple modules, FIGS. 4A-4D illustrate patch replacement using a single module and FIGS. 5A-5C illustrate module replacement on a patch. It is to be appreciated, however, that these use cases are presented by way of example only, and that embodiments are not limited solely to the specific examples shown in FIGS. 2A-2C, 3A-3E, 4A-4D and 5A-5C.

FIGS. 2A-2C show device replacement on a subject 200. The subject 200, as shown in FIG. 2A, has a first device 205a attached thereto. A second device 205b is shown attached to a charging station 215. The first device 205a is shown with a particular orientation 210a relative to a general coordinate system 210 shown in FIG. 2A. The general coordinate system 210 may be associated with an ideal sensing location and orientation, or be associated with some other type of reference coordinates (not necessarily associated with an ideal sensing location and/or orientation) for devices attached to the subject 200. Although not explicitly shown for clarity, one or both of the devices 205a, 205b may be in the form of patch/module pairs as described elsewhere herein.

In FIG. 2B, device replacement is illustrated in the change 225 wherein the second device 205b previously attached to the charging station 215 is now attached to the subject 200 at a particular location and orientation 210b as shown. After synchronization and coordination of the devices 205a, 205b, the first device 205a may be removed from subject 200 as shown by transition 250 in FIG. 2C, where the first device 205a previously attached to the subject 200 is instead attached to the charging station 215.

Synchronization, coordination or calibration of two or more devices may refer to calibrating a new device against an old device, such as by adjusting signals recorded by such devices to a mean, median or other comparative measure between the devices, adjusting signals recorded such that one or more of the devices having high noise profiles are calibrated to one or more other devices having lower noise profiles, etc.

The calibration may also facilitate increasing a device count, such as in using a plurality of devise for more robust monitoring of one or more physiological parameters of a subject. Such robust monitoring may include redundant monitoring, monitoring of physiological parameters from multiple perspectives (e.g., from different locations, using different types of sensors in a same or similar location, monitoring interrelated physiological parameters, allowing fault tolerance, etc.), providing higher order functionality (e.g., improving estimates, generating gradient assessments such as for water load distribution, heat flux, etc., generating higher order ECGs, EMG readings, etc., monitoring the same and different and/or interrelated parameters at different locations on a subject, etc.).

Increased functionality may be provided by monitoring with a plurality of devices, such as in the case of monitoring different but related parameters from multiple sites on a subject, such as in measuring an ECG on a chest of a subject with a first set of devices while also measuring pulse in one or more other devices on an extremity of the subject such as a wrist, finger, etc.

Monitoring different but related parameters may also be used in looking for timing differences between such signals in a subject. The use of multiple devices can also provide for simple and uninterrupted monitoring of a subject (i.e., with no down time).

Figure 3A:
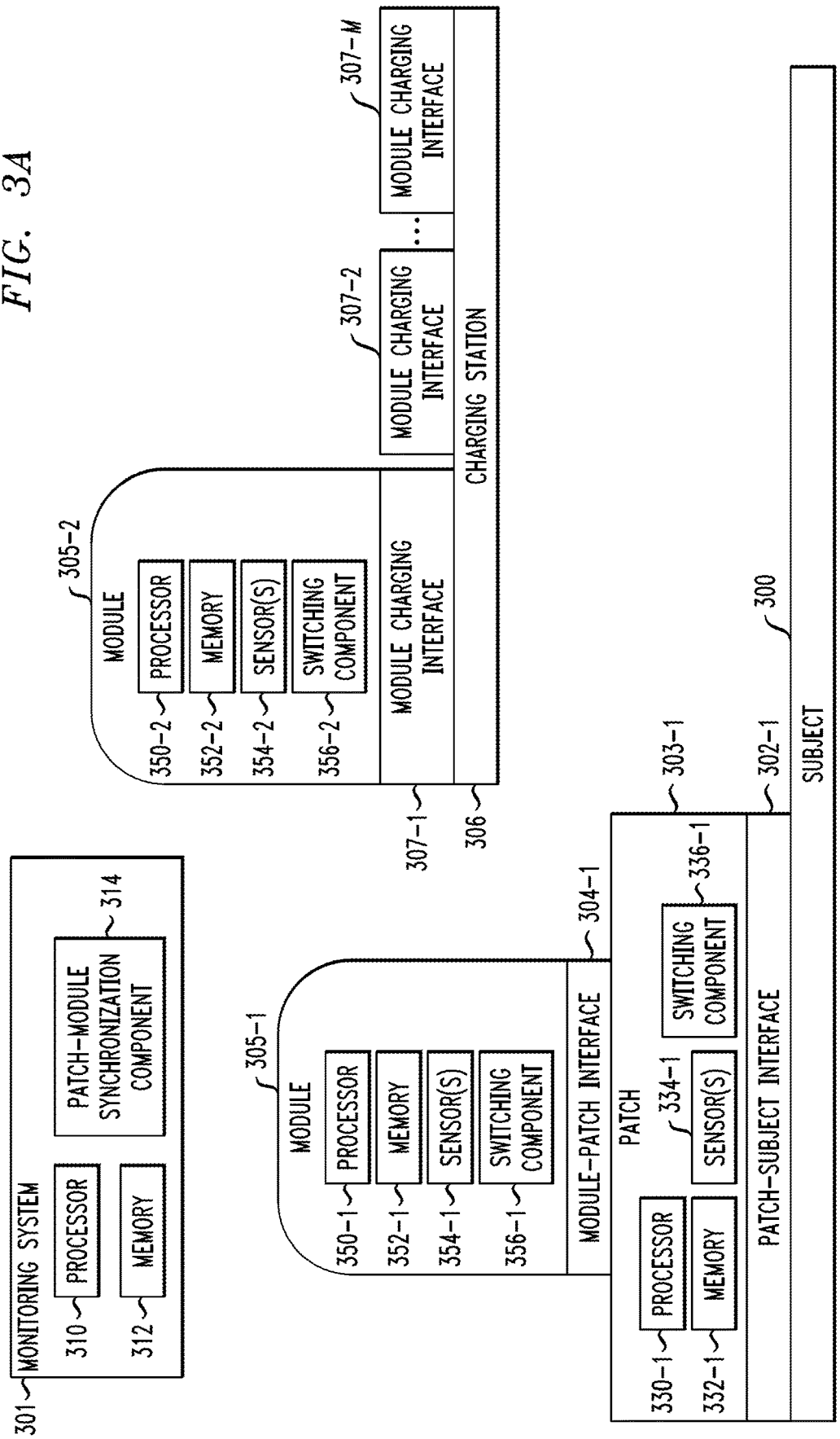
FIGS. 3A-3E illustrate patch replacement, according to an embodiment of the invention.
Figure 4B:
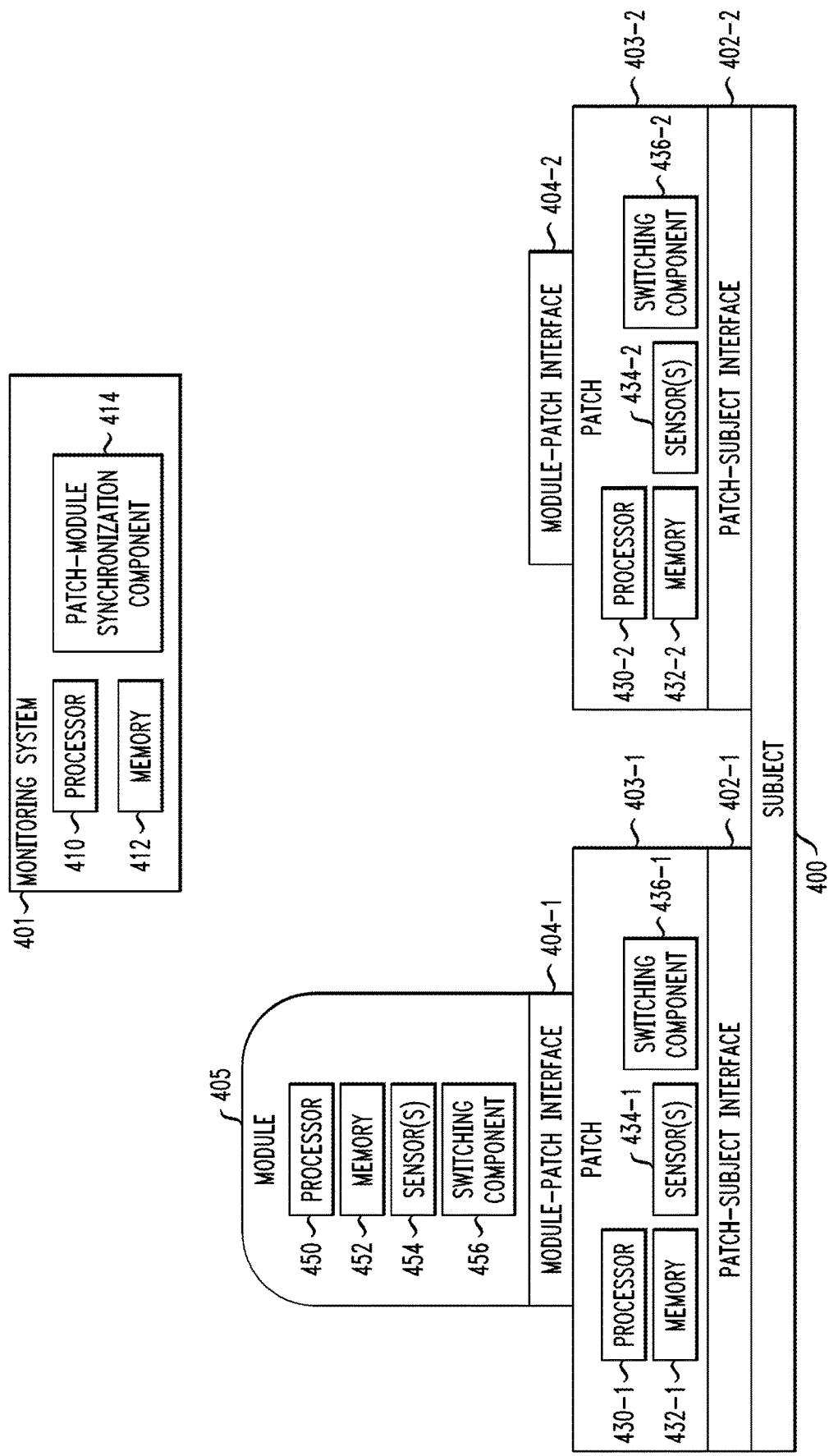

FIG. 3A shows a subject 300, a monitoring system 301, a patch-subject interface 302-1, a patch 303-1, a module-patch interface 304-1, modules 305-1 and 305-2, a charging station 306, and module charging interfaces 307-1, 307-2, . . . , 307-M In some embodiments, the host device described with respect to FIGS. 1A-1D may implement the monitoring system 301 and/or the charging station 306. This, however, is not a requirement. Although shown as being separate from the patch 303-1 and modules 305-1 and 305-2 in FIG. 3A, in some embodiments the monitoring system 301 may be implemented within or otherwise associated with one or more of the modules 305-1, 305-2 and the patch 303-1. The monitoring system 301, patch 303-1, modules 305-1, 305-2 and charging station 306 may be configured for communication with one another via network interfaces (not explicitly shown) facilitating communication over one or more wireless networks.

Monitoring system 301 includes a processor 310 and memory 312 implementing a patch-module synchronization component 314.

The processor 310 may comprise a microprocessor, a microcontroller, an application-specific integrated circuit (ASIC), a field-programmable gate array (FPGA) or other type of processing circuitry, as well as portions or combinations of such circuitry elements.

The memory 312 may comprise random access memory (RAM), read-only memory (ROM) or other types of memory, in any combination. The memory 312 and other memories disclosed herein may be viewed as examples of what are more generally referred to as "processor-readable storage media" storing executable computer program code or other types of software programs. Articles of manufacture comprising such processor-readable storage media are considered embodiments of the invention. A given such article of manufacture may comprise, for example, a storage device such as a storage disk, a storage array or an integrated circuit containing memory. The processor 310 may load the computer program code from the memory 312 and execute the code to provide the functionalities of the patch-module synchronization component 314.

The patch-module synchronization component 314 may, in some embodiments, provide functionality including but not limited to location coordination, maintaining continuity, improving bioimpedance monitoring, reducing artifacts during bioimpedance monitoring, etc.

Patch 303-1 includes a processor 330-1 and memory 332-1, which may be similar to the processor 310 and memory 312 described above with respect to the monitoring system 301.

Patch 303-1 also includes one or more sensors 334-1. The sensors 334-1 may include but are not limited to electric features, capacitive elements, resistive elements, touch sensitive components, analyte sensing elements, printed electrochemical sensors, light sensitive sensing elements, electrodes (including needle electrodes, ionically conducting electrodes, reference electrodes, etc.), electrical traces and/or interconnects, stretch sensing elements, contact interfaces, conduits, microfluidic channels, antennas, stretch resistant features, stretch vulnerable features (e.g., a feature that changes properties reversibly or irreversibly with stretch), strain sensing elements, photo-emitters, photodiodes, biasing features, bumps, touch sensors, pressure sensing elements, interfacial pressure sensing elements, piezoelectric elements, piezoresistive elements, chemical sensing elements, electrochemical cells, electrochemical sensors, redox reactive sensing electrodes, light sensitive structures, moisture sensitive structures, pressure sensitive structures, magnetic structures, bioadhesives, antennas, transistors, integrated circuits, transceivers, sacrificial structures, water soluble structures, temperature sensitive structures, light sensitive structures, light degrading structures, flexible light emitting elements, piezoresistive elements, moisture sensitive elements, mass transfer altering elements, etc. In some embodiments, one or more of the sensors 334-1 may have a controlled mass transfer property, such as a controlled moisture vapor conductivity so as to allow for a differential heat flux measurement through the patch 303-1, when such a region is used in conjunction with one or more temperature sensors in the patch 303-1, an attached module such as module 305-1, or the like.

The switching component 336-1 of patch 303-1, and may be implemented by processor 330-1 loading computer program code from memory 332-1 and executing the code to provide functionalities of the switching component 336-1.

The switching component 336-1 is configured to facilitate calibration of modules such as module 305-1 as well as to facilitate calibration between modules such as modules 305-1 and 305-2, and to facilitate replacement of one module, such as module 305-1, with another module, such as 305-2. The switching component 336-1 may operate in conjunction with the patch-module synchronization component 314 of the monitoring system 301 and/or a corresponding switching component in one or more of attached modules, such as switching component 356-1 of module 305-1. As described above, in some embodiments the functionality of the monitoring system 301 (e.g., functionality provided by the patch-module synchronization component 314) may be provided by the patch 303-1 and/or an attached module such as module 305-1. In such embodiments, the switching components 336-1 and 356-1 of the patch 303-1 and the attached module 305-1, respectively, may provide functionality described with respect to the patch-module synchronization component 314.

Although FIG. 3A and other figures shows patches which include processors, memories and switching components, patches do not necessarily need to include such elements. For example, in some use case scenarios patches such as patch 303-1 are designed to be low-cost and disposable, as well as flexible and comfortable to wear for subject 300. In such cases, it may be desired to provide patch 303-1 without one or more of the processor 330-1, memory 332-1 and/or switching component 336-1. It may also or alternatively be desired to reduce the number of or eliminate sensors 334-1 that are implemented in the patch. In some cases, one or more of such sensors may be implemented internal to an attached module such as module 305-1 rather than within the patch 303-1. Data collection, interconnection diagnostics and other functionality may preferably be implemented via module 305-1 rather than patch 303-1, with the patch 303-1 providing only sensors 334-1 and intimate body interfaces such as patch-subject interface 302-1 for electrophysiological access to subject 300 to reduce costs of the patch 303-1 as well as to provide simple, comfortable and disposable patches for attachment to subject 300. However, for use case scenarios where factors such as cost and wearability of the patch 303-1 are not as important, it may be preferred to provide the patch 303-1 as a reusable component or with additional hardware such as processor 330-1 and memory 332-1.

Patch 303-1, as shown in FIG. 3A, is attached to the subject 300 via patch-subject interface 302-1. The patch-subject interface 302-1 facilitates attachment of the patch 303-1 to the subject 300, and may include one or more adhesive layers. The patch-subject interface 302-1 may be single-use or multiple-use. Patch 303-1 is attached to module 305-1 via module-patch interface 304-1. The module-patch interface 304-1, in some embodiments, may include magnetic interconnects and/or mechanical features (including adhesives) that secure module 305-1 to patch 303-1.

Modules 305-1 and 305-2, as shown in FIG. 3A, include respective processors 350-1, 350-2, memories 352-1, 352-2, sensors 354-1, 354-2 and switching components 356-1, 356-2, which may be similar to the processor 330-1, memory 332-1, sensors 334-1 and switching component 336-1 of patch 330-1.

Also shown in FIG. 3A is charging station 306, including a number of module charging interfaces 307-1, 307-2, . . . , 307-M The particular number M of module charging interfaces may vary as desired for a particular use case. For example, in some embodiments a subject may have multiple patch-module pairs attached thereto, and the charging station 307 may include a number of module charging interfaces to provide for charging one or more backup modules for each of the patch-module pairs. Alternatively, the charging station 306 may include only a single module charging interface. Each of the module charging interfaces 307 facilitates attachment of a module to the charging station 306. As shown, module 305-2 is attached to charging station 306 via module charging interface 307-1. In some embodiments, one or more of the module charging interfaces 307 may include a wireless charging feature, such as a feature permitting charging of a module via inductive charging. In other embodiments, one or more of the module-charging interfaces 307 may provide for mechanical attachment of a module to the charging station 306, such as via one or more wires or mating electrical interfaces.

Although not explicitly shown in FIG. 3A, one or more of the monitoring system 301, patch 303-1, modules 305-1, 305-2, and charging station 306 may be configured to provide indications to a user. The charging station 306 and/or modules 305-1, 305-2, for example, may include one or more indicators (e.g., visual indicators, audio indicators) that display or output a notification indicative of the charging status of a module attached thereto. For example, the indicators may indicate whether a module is charging or not charging, or may provide more detailed information such as a charge level of a module (e.g., a percentage, battery life remaining, or other visual indication of the charge level of a module).

The monitoring system 301 (or the patch 303-1, modules 305-1, 305-2 or charging station 306) may also or alternatively generate indications that instruct the user as to the timing of and/or location of attachment of devices to a subject. For example, the monitoring system 301 may generate an indication that monitoring is to begin and that a first patch/module pair (or more generally a device) is to be attached to the subject 300. This indication may provide location information (which may include orientation information) regarding an attachment site for the first patch/module pair. After the end of a first monitoring period, the monitoring system 301 may generate another indication that a transitionary monitoring period is to begin. This indication may provide location information for attachment of a second patch/module pair to the subject 300. At the end of the transitionary monitoring period, another indication may be generated indicating that the first patch/module pair is to be removed from the subject 300.

In some embodiments, different ones of the module charging interfaces 307 may be configured for attachment to different types of modules. Different modules may be used to monitor different types of information, or be configured for attachment to different types of patches. A single charging station, such as charging station 306, may include module charging interfaces for multiple different types of modules or may include module charging interfaces for only a single type of module.

It should be appreciated that the use of charging station 306 is optional. In some embodiments, for example, modules 305-1 and 305-2 may not include rechargeable power sources such as batteries and thus the charging station 306 may not be necessary.

FIG. 3A shows the state of a system prior to a swap initiation event. A swap initiation event may include, for example, detecting one or more triggering conditions associated with the module 305-1, such as detecting a low battery life of the module 305-1 attached to the patch 303-1, detecting one or more designated failure conditions in the module 305-1 attached to the patch 303-1, detecting that the memory 352-1 of the module 305-1 is full, detecting that a new or upgraded module such as module 305-2 is available, detecting expiration of a designated time period, detecting a user request to initiate hot-swapping the module 305-1 attached to the patch 303-1, etc. In some cases, hot-swapping the module 305-1 may also include hot-swapping the patch 303-1. For example, in cases wherein the useful life of a module such as module 305-1 is less than that of patch 303-1, it may be more efficient to replace the patch 303-1 in addition to replacing module 305-1 due to the low cost of a patch and/or the ease of transition. Thus, replacing the module 305-1 may include replacing the patch 303-1 as well, such is in cases where patches such as patch 303-1 are meant to be cost-effective disposable components. Alternatively, the new module 305-2 may be hot-swapped onto the same patch 305-1, such as using techniques described below with respect to FIGS. 5A-5C.

A swap initiation event may also include, for example, detecting one or more triggering conditions associated with the patch 303-1, which may be analogous to the triggering conditions associated with module 305-1. For example, triggering conditions associated with patch 303-1 include but are not limited to detecting low battery life of the patch 303-1 (if the patch includes a battery or other power source), detecting one or more designated failure conditions in the patch 303-1 (such as detecting that one or more of the sensors 334-1 is failing), detecting expiration of a designated time period, detecting a user request to initiate hot-swapping of the patch 330-1, etc.

In response to detecting a swap initiation event, one or more of the switching components 336-1, 356-1 and patch-module synchronization component 314 can initiate hot-swapping as described elsewhere herein. Hot-swapping may be initiated, for example by sending a notification (e.g., a text message, email, page, etc.) to a user, the subject, a nurse, etc. Alternatively, hot-swapping may be part of a scheduled event, such as part of a nurse's daily routine on the floor in a hospital.

Figure 3B:
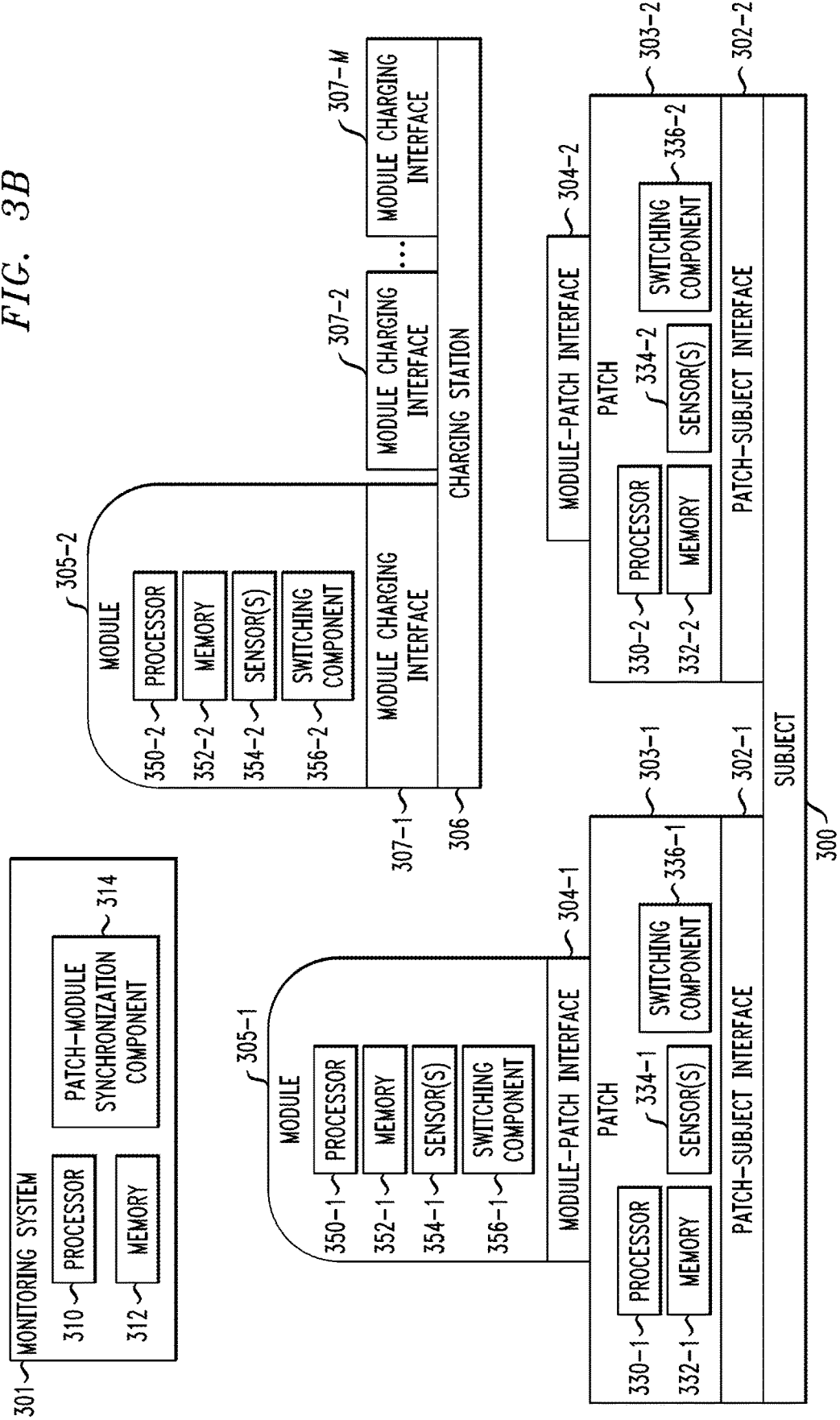

FIG. 3B shows the system of FIG. 3A following attachment of another patch 303-2 to the subject 300. The patch 303-2 is configured in a manner similar to that of patch 303-1, including a processor 330-2, memory 332-2, one or more sensors 334-2 and a switching component 336-2. Patch 303-2 is attached to subject via patch-subject interface 302-2, which may be similar to the patch-subject interface 302-1 described above. The patch also includes a module-patch interface 304-2, which may be similar to the module-patch interface 304-1.

Patch 303-2 may be attached to the subject 300 in response to a swap initiation event to replace the patch 303-1. Alternatively, the patch 303-2 may be attached to the subject 300 for redundancy, without necessarily replacing patch 303-1.

Figure 3C:
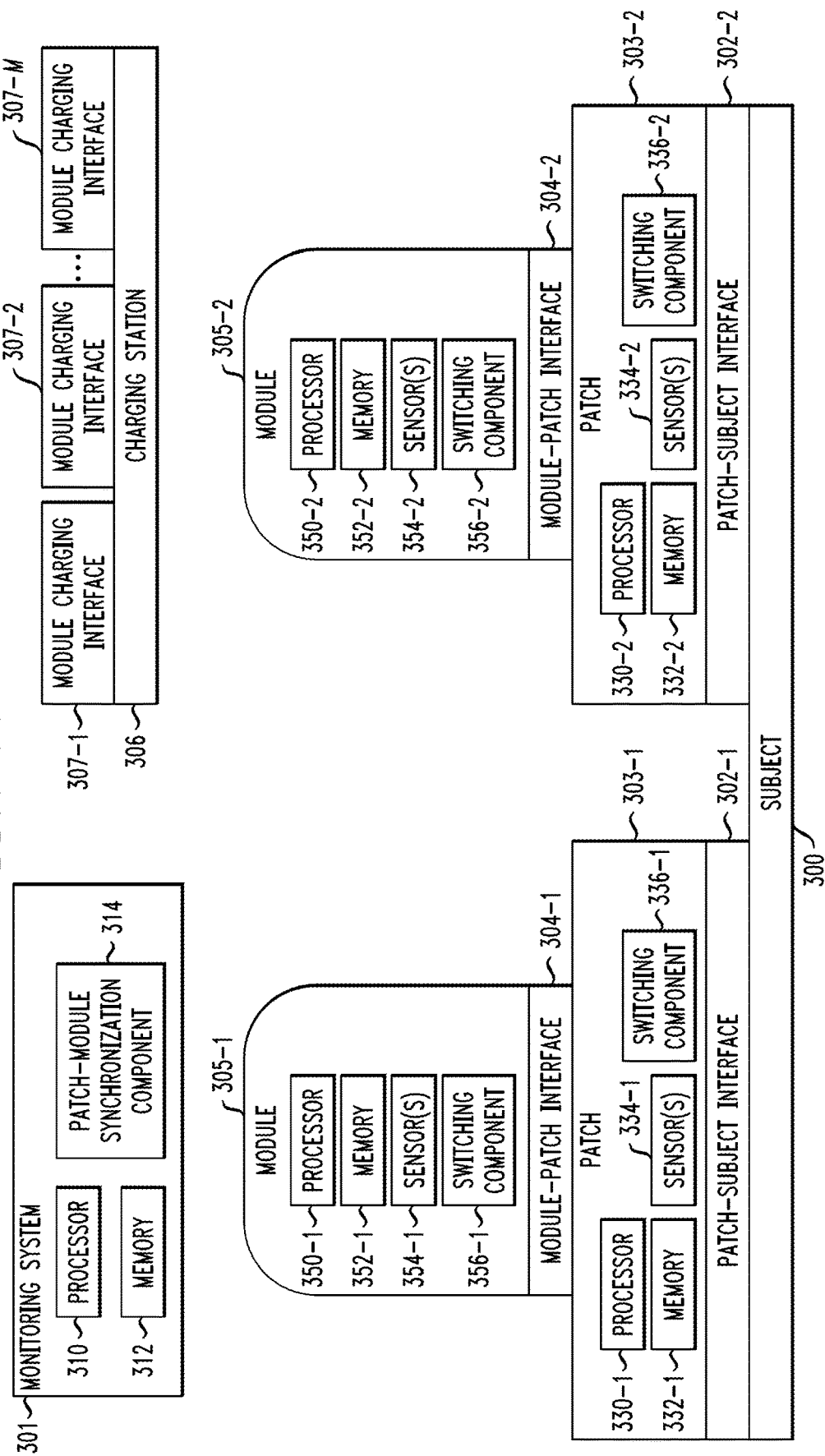

FIG. 3C shows the system of FIG. 3B following attachment of module 305-2, previously attached to the charging station 306 via module charging interface 307-1, to the patch 303-2 via module-patch interface 304-2. Once attached, a transitionary period of monitoring may proceed where both modules 305-1 and 305-2 monitor or measure one or more physiological parameters of the subject 300 to coordinate synchronization or calibration of the new module 305-2 attached to the new patch 303-2.

Figure 3D:
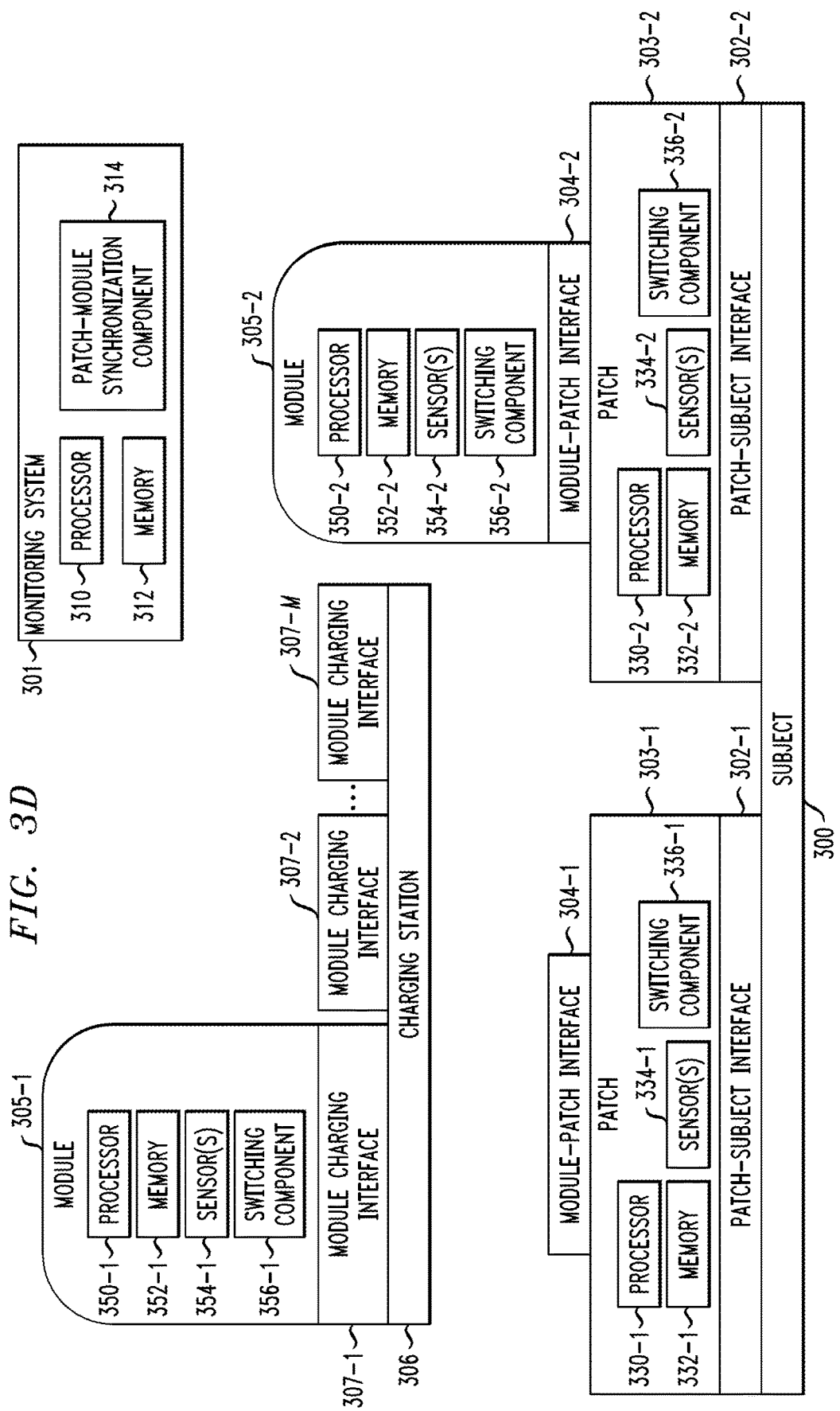

FIG. 3D shows the system of FIG. 3C after the transitionary period, where the module 305-1 is removed from patch 303-1 and attached to the charging station 306 via module charging interface 307-1. It is to be appreciated, however, that the old module 305-1 need not be attached to the charging station 306 following removal from the patch 303-1. For example, in some cases modules may be disposable and thus may be discarded, possibly after reading or downloading any data stored therein to the monitoring system 301 or a data store. In other cases, the modules may not be disposable but the particular module 305-1 removed from the patch 303-1 may have reached end-of-life status (e.g., the module 305-1 removed from the patch 303-1 may be an older version module that will not be used in the future, the module 305-1 may be removed due to a defect or other failure condition, etc.) or may not be further used for a continuous monitoring session of the subject 300 (e.g., in a continuous monitoring session there may be distinct types of modules that are attached to the subject 300 in different phases).

Figure 3E:
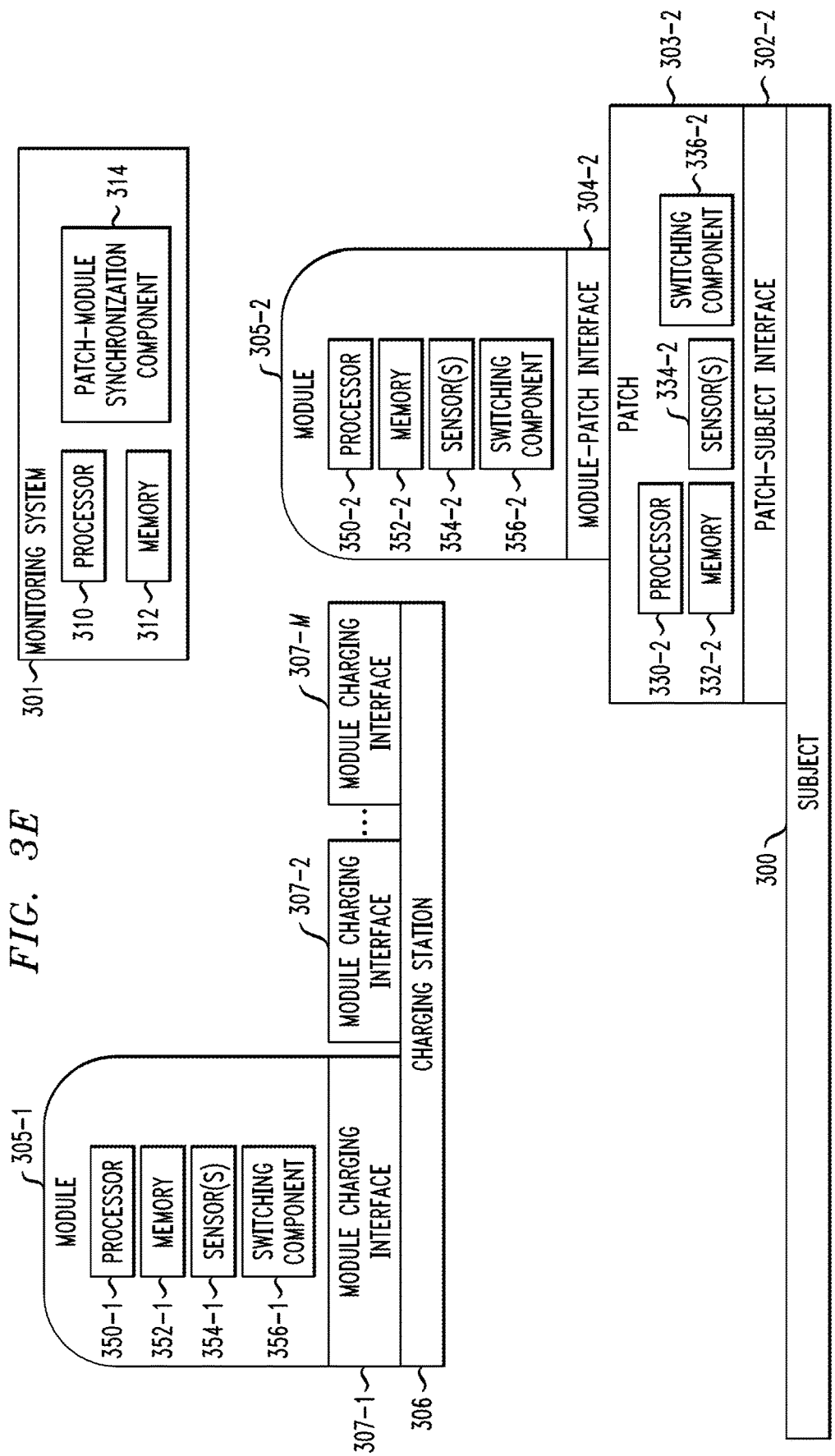

FIG. 3E shows the system of FIG. 3D following removal of the patch 303-1 from the subject 300. In some cases, the patch 303-1 may be discarded after removal from subject 300. In other cases, the patch 303-1 may be recycled for reuse later in the continuous monitoring session of the subject 300, or for use in monitoring another subject or in another monitoring session of subject 300. In some cases charging station 306 may be provide one or more interfaces for attaching patches to be charged or recharged before attachment to subject 300.

FIGS. 3A-3E illustrate an example wherein there are multiple patches and multiple modules. FIGS. 4A-4D illustrate an example wherein there are multiple patches but a single module. FIG. 4A shows a subject 400, monitoring system 401, patch 403-1 and module 405.

Monitoring system 401, similar to monitoring system 301 shown in FIGS. 3A-3E, includes a processor 410, memory 412 and patch-module synchronization component 414.

Patch 403-1 is shown attached to subject 400 via patch-subject interface 402-1. The patch 403-1, similar to patches 303-1 and 303-2 shown in FIGS. 3A-3E, includes a processor 430-1, memory 432-1, one or more sensors 434-1 and a switching component 436-1.

Module 405 is attached to the patch 403-1 via module-patch interface 404-1. The module 405, similar to modules 305-1 and 305-2 shown in FIGS. 3A-3E, includes a processor 450, memory 452, one or more sensors 454 and a switching component 456.

FIG. 4A shows the state of a system prior to a swap initiation event. Swap initiation events in this system relate to designated conditions of the patch 403-1, as there is only one module 405. The patch-module pair formed from patch 403-1 and module 405 may be configured to monitor one or more physiological parameters of a subject 400 over time. Periodically, in response to a user request, a designated failure condition or other swap initiation event, the patch interfacing the module 405 with the subject 400 may be replaced.

FIG. 4B shows the system of FIG. 4A following attachment of a second patch, patch 403-2, to the subject 400 via patch-subject interface 402-2. The patch 403-1, similar to patch 303-1, includes processor 430-2, memory 432-2, one or more sensors 434-2 and switching component 436-2. During this time (either before or after attachment of the patch 403-2), the module 405 may enter into a transitionary period where it buffers data in its internal memory 452, in memory 412 of monitoring system 401, or possibly in one or both of the memories 432-1, 432-2 of patches 403-1 and 403-2. The buffered data may be used by the module 405 to synchronize the module 405 with patch 403-2.

Figure 4C:
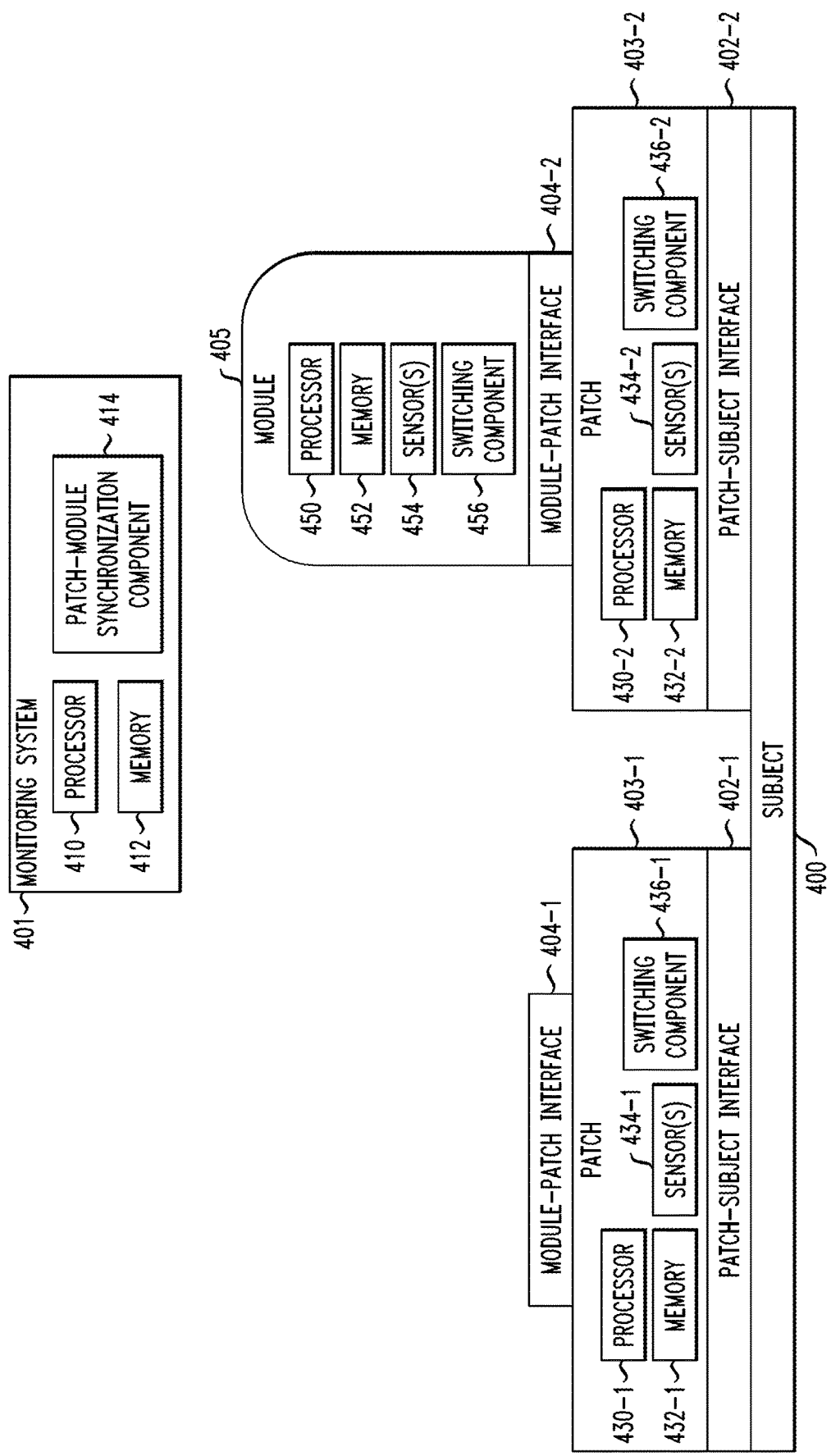
Figure 4D:
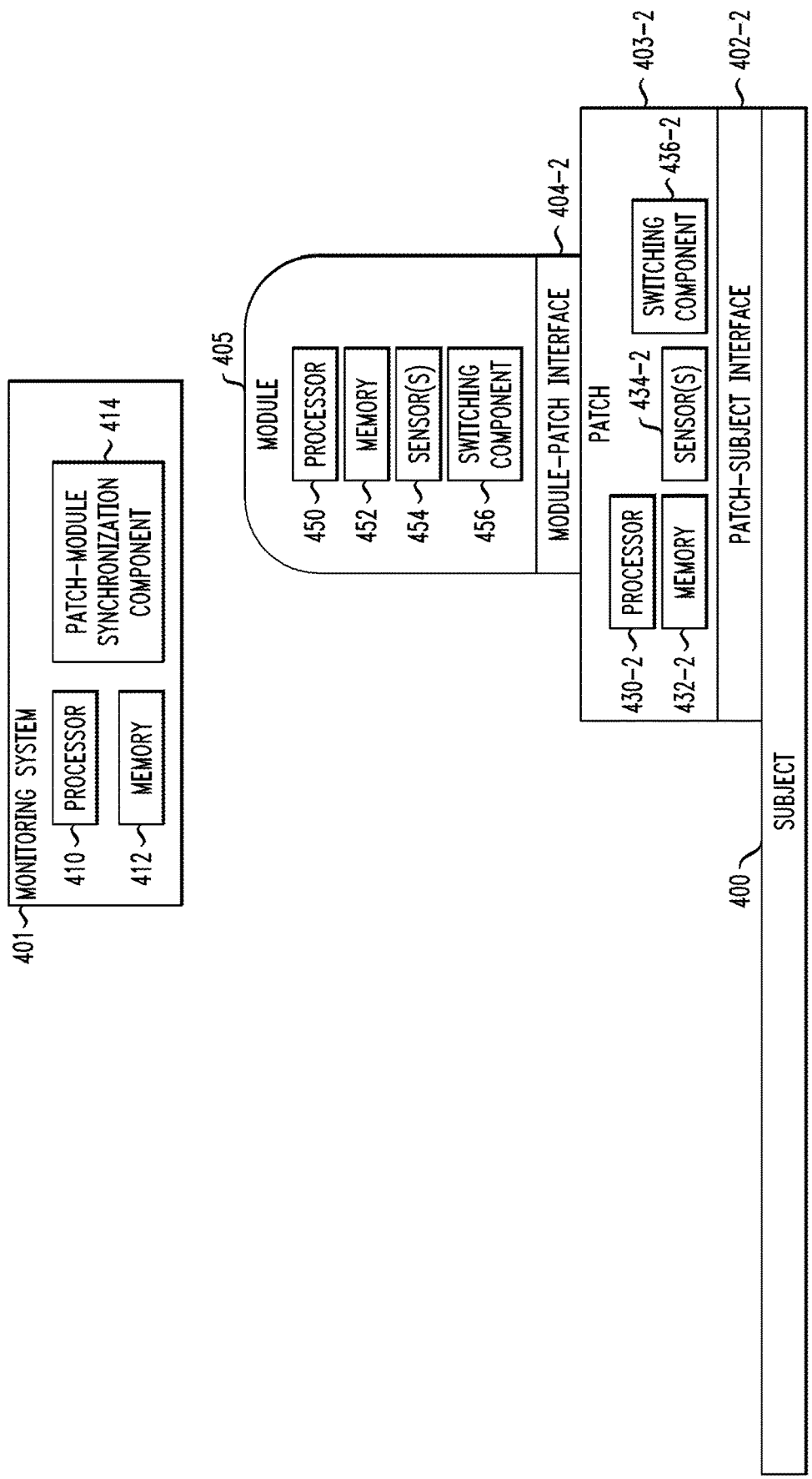
Figure 5A:
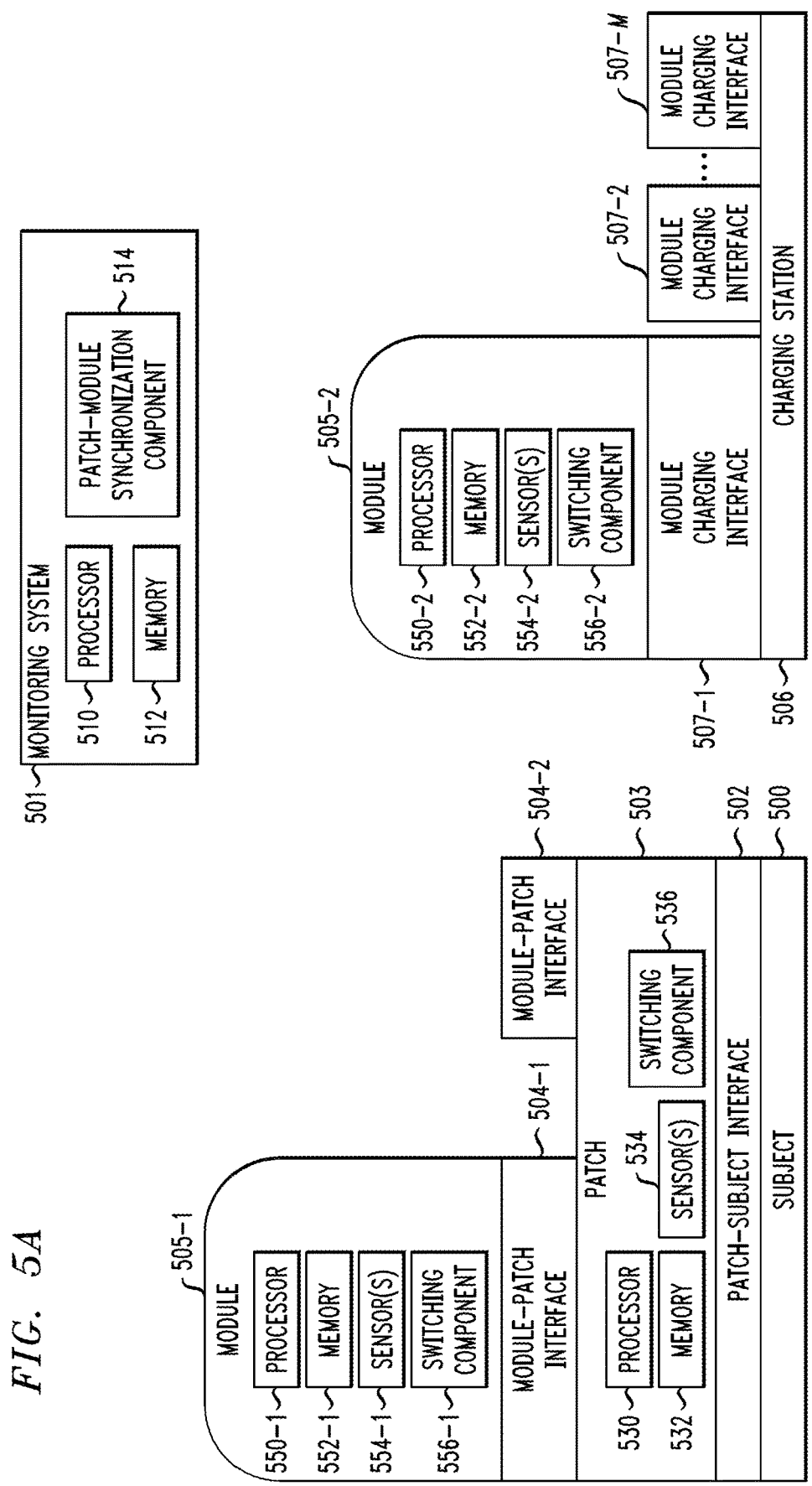
FIGS. 5A-5C illustrate module replacement, according to an embodiment of the invention.
Figure 5B:
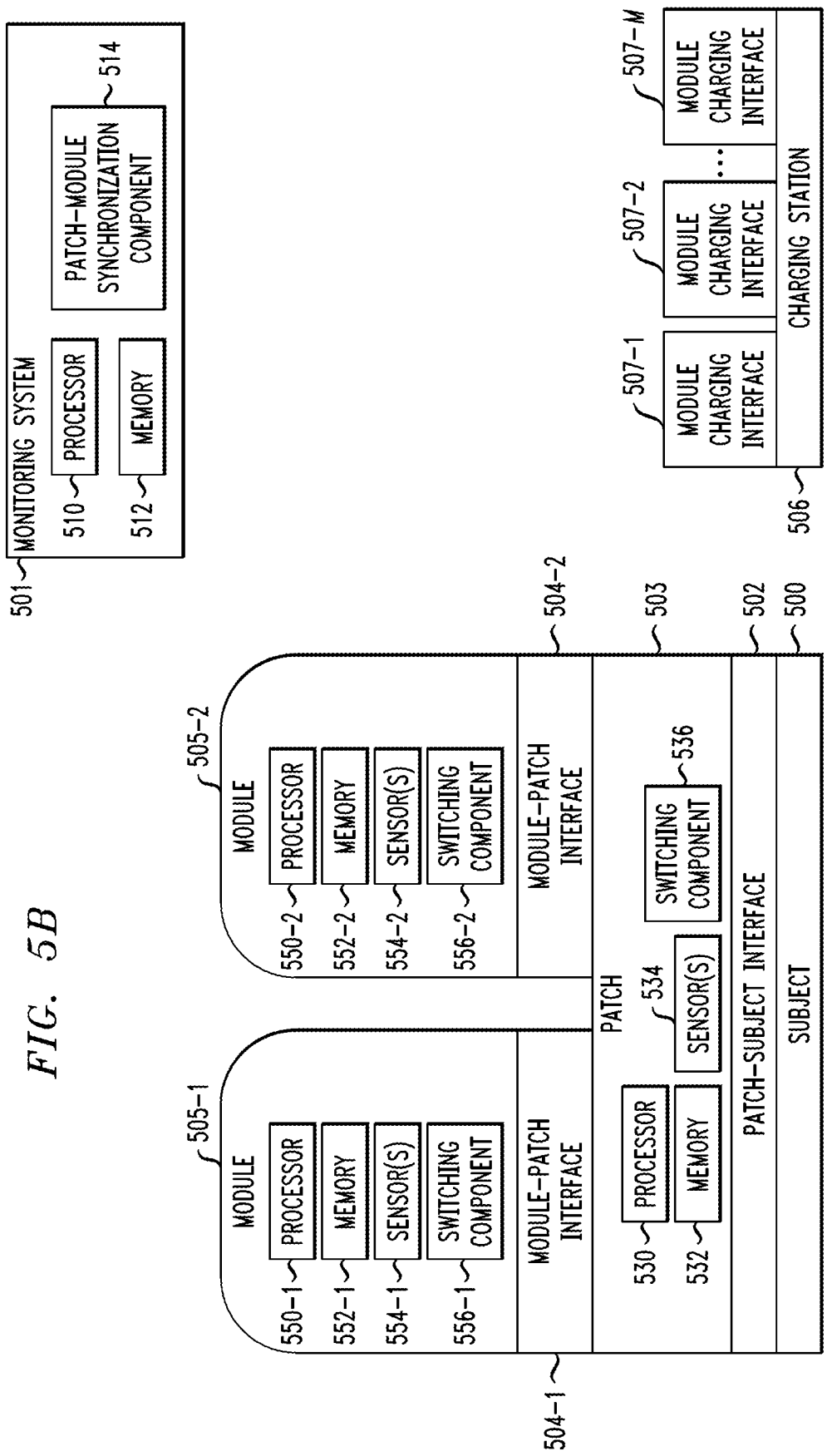
Figure 5C:
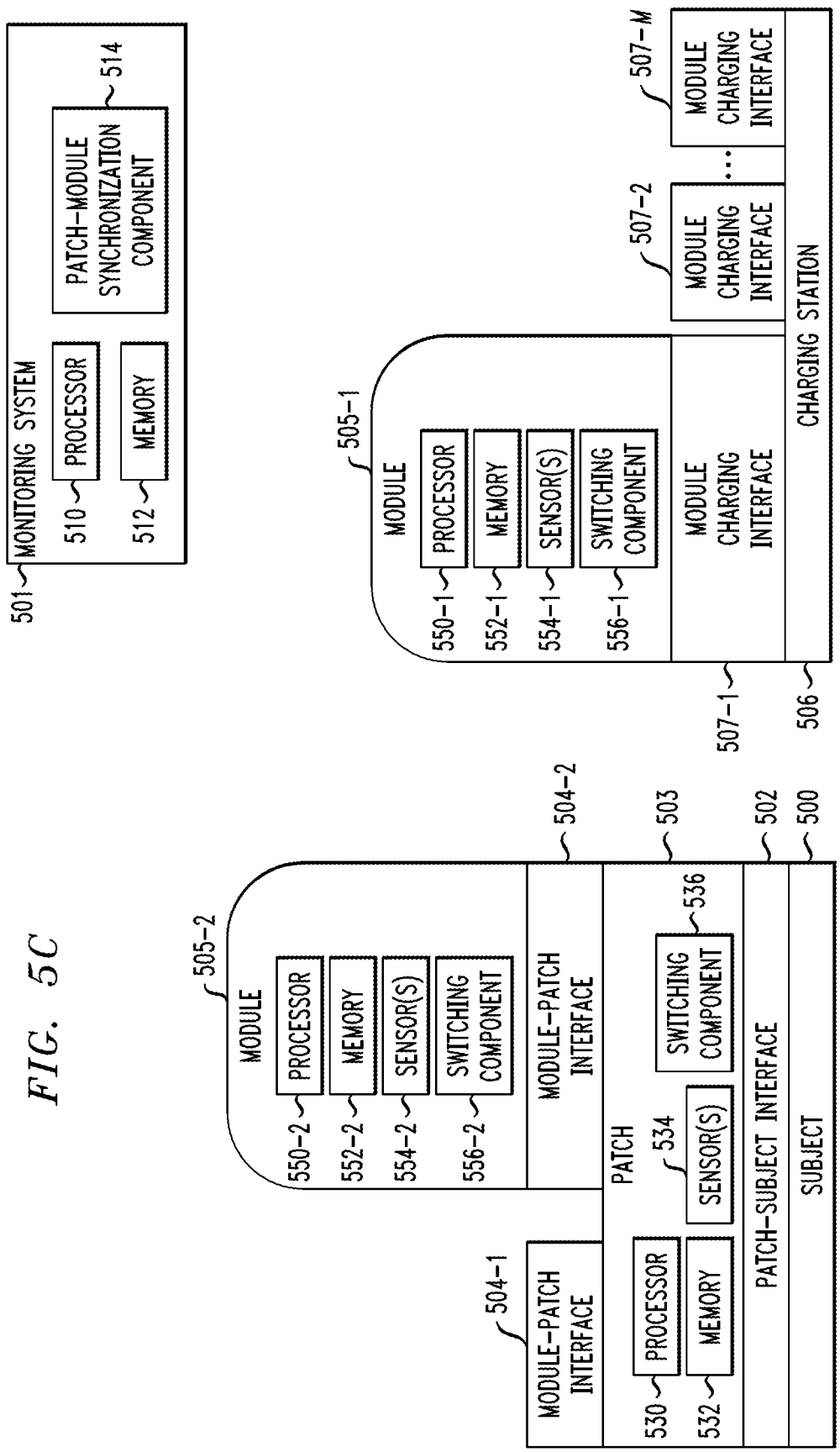

FIG. 4C shows the FIG. 4B system after the module 405 is moved from the patch 403-1 to the patch 403-2. FIG. 4D shows the FIG. 4C system after the patch 403-1 is removed from the subject 400.

Although FIGS. 3A-3E and FIGS. 4A-4D illustrate arrangements in which each patch 303-1, 303-2, 403-1, and 403-2 includes a single module-patch interface (304-1, 304-2, 404-1, and 404-2, respectively), embodiments are not limited to these arrangements. In other embodiments, a patch may include multiple module-patch interfaces. Such configurations may be used, for example, in facilitating the attachment of different types of modules to a subject using a single patch. Additionally or alternatively, such configurations may be used in situations wherein the life cycle of a patch is expected to exceed the life cycle of a module, such as a situation in which a patch is configured for use for a period of multiple days but for which modules attached to the patch have a battery life less than the life cycle of the patch, such as only a single day.

FIGS. 5A-5C illustrate an example wherein a patch has multiple module-patch interfaces. FIG. 5A shows a system include a subject 500, monitoring system 501, patch-subject interface 502, patch 503, module-patch interfaces 504-1 and 504-2, modules 505-1 and 505-2 and a charging station 506 with module charging interfaces 507-1, 507-2, . . . , 507-M.

The monitoring system 501 may be configured in a manner similar to that of monitoring system 301 shown in FIGS. 3A-3E, and includes processor 510, memory 512 and patch-module synchronization component 514.

Patch 503 may be configured in a manner similar to that of patches 303-1 and 303-2 shown in FIGS. 3A-3E, including a processor 530, memory 532, one or more sensors 534 and switching component 536. Patch 503, however, differs from patches 303-1 and 303-2 in that it includes two module-patch interfaces 504-1 and 504-2. It is important to note that although FIGS. 5A-5C show an example of a patch with two module-patch interfaces 504-1, 504-2, a patch may more generally include any desired number of module-patch interfaces, including module-patch interfaces of different types facilitating attachment of different types of modules.

Modules 505-1 and 505-2 may be configured in a manner similar to that of modules 305-1 and 305-2 shown in FIGS. 3A-3E, and include respective processor 550-1, 550-2, memories 552-1, 552-2, sensors 554-1, 554-2 and switching components 556-1, 556-2.

Charging station 506 may be configured in a manner similar to that of charging station 306 shown in FIGS. 3A-3E, including a number of module charging interfaces 507-1, 507-2, . . . , 507-M.

FIG. 5A shows the state of a system prior to a swap initiation event, such as a swap initiation event indicating that module 505-1 is to be replaced. Alternatively, FIG. 5A may also be considered as showing a state of a system wherein a first module, 505-1, is calibrated to subject 500 and a second module, 505-2, is to be attached to the subject 500 for redundancy or to monitor different physiological parameters of subject 500 and not necessarily to replace the module 505-1.

FIG. 5B shows the FIG. 5A system following the swap initiation event, wherein the module 505-2 is moved and attached to the patch 503 via module-patch interface 504-2. Once attached, a transitionary monitoring period may commence as described above. Following the transitionary period, the module 505-2 may be synchronized or calibrated to the module 505-1. Once synchronized or calibrated, the module 505-1 may be removed from the patch 503 as shown in FIG. 5C. While FIG. 5C shows the module 505-1 being attached to the charging station 506 via module charging interface 507-1, this is not a requirement. In some cases, the module 505-1 may be discarded or recycled.

In some embodiments, different modules attached to one or more patches on a subject may provide for redundancy. In other embodiments, different modules attached to a patch or subject may provide different functions (in addition to or in place of providing redundancy). For example, each of the modules attached to one or more patches on a subject may be configured with different types of sensors, or may be configured so as to monitor different physiologic parameters of the subject, possibly for use in different phases of a long-term continuous monitoring session.

Although FIGS. 3A-3E, 4A-4D and 5A-5C show examples wherein one patch is attached to a subject, and either that patch or a module thereto is to be hot-swapped, this is solely for clarity of illustration. In other embodiments, multiple patches may be attached to a subject as shown and described with respect to FIGS. 1A-1D and FIGS. 2A-2C. Hot-swapping of patches and/or modules may occur contemporaneously for multiple patches and/or modules. For example, in some embodiments multiple patches may be attached to a subject, and the modules attached to such patches may be periodically swapped to new patches. The modules may be swapped in a staggered manner (e.g., such that only one module hot-swap occurs at a given time), in a partially overlapping manner (e.g., such that multiple modules are hot-swapped although such hot-swapping is not coordinated such that a first module hot-swap may be completed before a second module hot-swap), or in a coordinated manner (e.g., such that two or more modules are hot-swapped substantially at the same time). In addition, for patches with multiple patch-module interfaces, multiple modules may be swapped in a staggered, partially overlapping or coordinated manner.

In embodiments wherein a patch includes multiple module-patch interfaces, each module-patch interface may be single-use (e.g., removal of a module from a patch may cause irreversible damage to the associated patch-module interface, such as in a case where the module-patch interface is an adhesive layer) or multiple-use.

During swapping events, modules and/or patches may exchange buffered data when they are brought in close proximity to one another, such as using near field communication (NFC) or other short-range wireless interfaces. Such transfer of buffered data need not necessarily occur while both patches and/or modules are connected to a subject or charging station. For example, when replacing a first module, a second module may be brought in proximity to the first module to receive buffered data before placement or attachment of the module to a patch on a subject.

Figure 6:
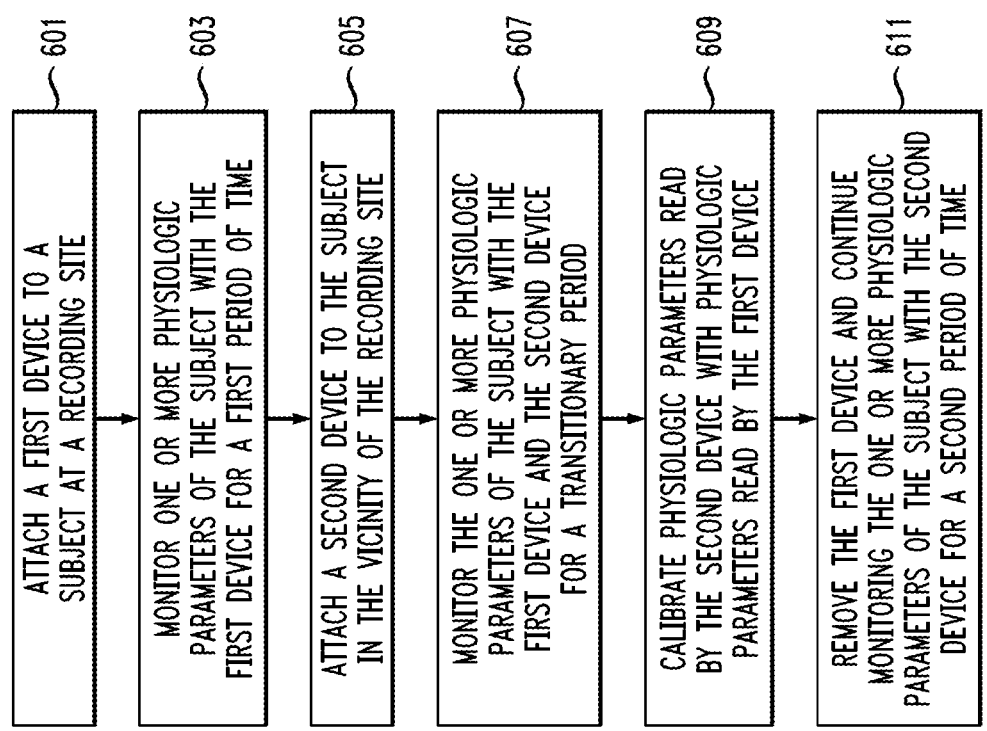
FIG. 6 illustrates a flow diagram of a process for device replacement, according to an embodiment of the invention.

FIG. 6 illustrates a process for hot-swapping. The method begins with step 601, attaching a first device, such as a module and/or patch disclosed herein, to a subject at a recording site. In step 603, one or more physiologic parameters of the subject are monitored with the first device for a first period of time. Next, in step 605, a second device, such as another module and/or another patch, is attached to the subject in the vicinity of the recording site. In step 607, the one or more physiologic parameters of the subject are then monitored for a transitionary period using both the first device and the second device. In step 609, the physiologic parameters read by the second device are calibrated with physiologic parameters read by the first device, and then in step 611 the first device is removed from the subject and monitoring of the one or more physiologic parameters of the subject is continued with the second device for a second period of time. In some embodiments, step 611 may not include removing the first device from the subject, such as in cases where the second device is used for redundancy rather than to hot-swap or replace the first device.

Figure 7:
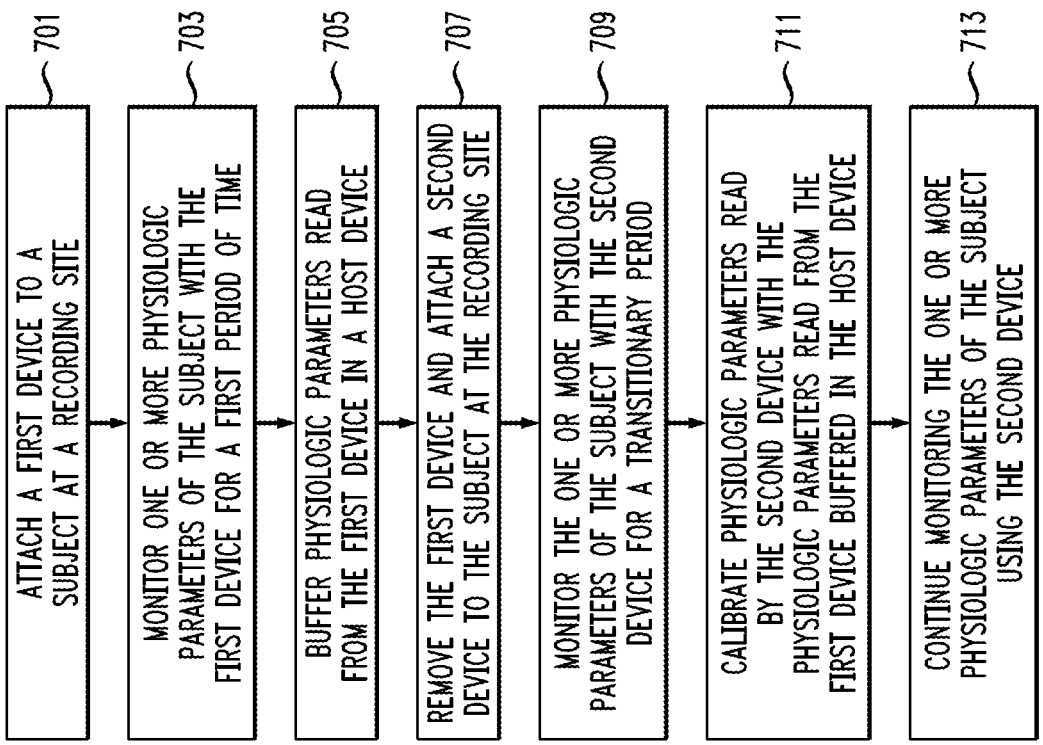
FIG. 7 illustrates a flow diagram of another process for device replacement, according to an embodiment of the invention.

FIG. 7 illustrates another process for hot-swapping. The method begins with step 701, attaching a first device to a subject at a recording site. The first device may be, for example, a patch and/or module as disclosed herein. In step 703, one or more physiologic parameters of the subject are monitored with the first device for a first period of time. The physiologic parameters read from the first device are then buffered in a host device in step 705. In some embodiments, the first device may be a patch and the host device is the module, or vice versa. In other embodiments, the host device may be a monitoring system or other device external to the host device (e.g., external to both a patch and a module attached thereto). In step 707, the first device is then removed from the subject and a second device, such as a patch and/or module as disclosed herein, is attached to the subject at the recording site. In step 709, the one or more physiologic parameters of the subject are then monitored with the second device for a transitionary period. In step 711, the physiologic parameters read by the second device are calibrated using the physiological parameters previously read from the first device that are buffered in the host device. Monitoring of the one or more physiologic parameters then continues using the second device in step 713.

Embodiments provide methods for maintaining continuity and consistency of measurement during prolonged monitoring of physiologic, kinematic, and/or proprioceptive signals from a subject. Such methods may be used, for example, to maintain temporal signal continuity during a transition from a worn to a fresh device, to limit downtime due to battery charging, to maintain consistency of measure of relative and subjective signals including but not limited to muscle selective electromyography, somatosensory functions, tissue hydration, water retention, local tissue strain, and relationships between such values and movements, posture, or the like, etc. Methods described herein may utilize a multifactor approach, integrating a series of physiologic responses to stimuli that provide real-time processing and sensor feedback over long periods of time.

Various devices and methods described herein may provide one or more advantages in a number of different use cases. For example, assume that it is desired to measure some physiologic parameters on a subject for three weeks. In this case, one can attempt to design a system to last three weeks, the full monitoring period. This may not be desired, however, as adhesives and patches can get worn out, ratty or otherwise degraded in much less than three weeks even with suggested use. As an alternative, using one or more methods described herein, a system is designed to utilize cost effective patches that can be worn for a few days at a time. Various automated ways may be used to determine when to change a patch, such as in response to swap initiation events described above. After a first monitoring period with a first patch, a new patch and/or module can be placed on the subject to continue the monitoring process to replace the first patch. During transition from one patch to another, however, key information may be lost that can make long-term tracking of such information challenging. By transitioning "early" (e.g., while both devices are attached to a subject during the above-described transitionary monitoring period), it is possible to simultaneously analyze the same physiologic response from slightly different sites to better correlate responses from multiple devices. Thus, when the first device (such as a patch/module pair) is removed, monitoring can continue with a new device with better correlation in the data being monitored.

Methods described herein may be used for monitoring various types of physiologic parameters, including but not limited to electromyography, impedance spectroscopy, continuous glucose monitoring, stretch monitoring, electrocardiography, optical tissue monitoring, and the like.

In one or more of these any other applications, variations associated with readings may occur when transitioning from sensing a parameter at a first sensing location to sensing that parameter at a new, second location. Such variations may occur even if the first and second sensing locations are located near the same site on the body of a subject. Variations may relate to differences associated with the actual location of the new site versus the old site, differences in tissue properties under the new site versus the old site, differences in coupling of a sensing device at the new site versus a sensing device at the old site, differences in bias pressure under the new device versus the old device, differences in electrical and/or mechanical properties of the new device versus the old device, and the like. Such variability may increase challenges associated with correlating the function of the intended physiologic parameter(s) from an old device to a new device, and/or reliably extracting a trend in a physiologic function over long periods of time. Such issues may relate to long term prediction of thoracic water load (e.g., edema), muscle activity (e.g., diaphragmatic exertion and/or depth, bicep exertion and/or depth, etc.), glucose levels and trends, tissue strain and strain baseline readings, cardiac function, tissue perfusion, microvascular dilation, somatosensory function, sudomotor function, and the like.

Described below is a method for compensating for position-related changes in monitoring, also referred to herein as location coordination functionality. Depending on application, such as the particular physiologic parameters being monitored (e.g., ECG, EMG, EEG, SMA, somatosensory response, respiration, peripheral sp02, water load, hydration, glucose, etc.), there may be variations to the general method detailed below. Such variations may be related to differences in magnitude in a recorded physiologic signal, phase delay between recording sites, differences in the character of the signal (e.g., changes in the wave contributions of an ECG to the overall recorded signal), changes in the action potentials recorded at different sites, changes in the offset of the recorded signal, changes in the frequency spectral content of the recorded signal, and the like. The correlation between such variations during simultaneous recording from multiple devices may be used to generate a transfer function and/or correction factor(s) to minimize the variations in the recording when moving from the first recording device to the next one.

Locational variations due to device placement may register as changes in a signal under measurement. For example, an ECG represents measurements of the 3D electrical field generated by heart tissues, and is dependent upon where in that 3D field the measurements are being made. In this context, variations are not necessarily related to the timing of different waves seen at the recording site, but instead may be related generally to differences in terms of amplitudes, relative relationships between different waves in a recorded signal, etc. For example, an application may look for ST segment depression/elevation, p-wave amplitude changes, etc. The act of placing a new device (such as a patch/module pair of the type described herein) at a location away from an original device may affect such readings, irrespective of device-specific variations in recording properties.

Changes in the character of an ECG may be used to generate necessary correlations between old and new devices. In the context of an ECG, generating such correlations may proceed as described below. Feature extraction of wave components from ECGs may be obtained from first and second devices. This feature extraction may include, but is not limited to, P height, P polarity, Q height, Q polarity, QRS max, ST height, ST polarity, T height, T polarity, baseline noise, baseline wander arrival time, the character (e.g., shape) of any such waves, the relative ratios of any such waves to each other, beat classification, average ECG construction, etc. Such assessments or feature extraction may be made on a beat-by-beat basis and/or on an average ECG (e.g., the average ECG constructed from data collected over the transitionary monitoring period or some subset thereof).

The ST segment represents the initial phase of ventricular repolarization. Changes in the ST segment elevation and/or depression, beyond a baseline, may be an indication of a serious pathology that indicates an imminent risk for a subject. When a second device is placed onto the subject, the ST segment elevation/depression will generally be somewhat different that that measured by a first device, due in part to locational changes in where recordings are being made. By correlating the ST segment elevation/depression recorded by the second device with that recorded by the first device during a transitionary recording period, the confidence with which changes can be assessed before and after the transitionary period is increased. It is important to note that, during the transitionary recording period, the first and second devices simultaneously record one or more physiologic parameters of the subject, such as an ECG from which features such as ST segment elevation/depression may be extracted. Without the transitionary period, there may be questions as to whether a new recording site (e.g., the recording site of the second device) is a poor recording site for capturing ST segment elevation/depression, whether ST segment elevation/depression has changed, etc. The transitionary period is useful in determining correlations and synchronizing the first and second devices, such as determining how relative changes in ST segment elevation/depression (or one or more other features extracted from a recording of a physiologic parameter of a subject) at a new site correlate with that of the previous site.

In some embodiments, location coordination or correlation, including 3D location correlation, may be enhanced with use of a pre-recorded map. The pre-recorded map may be generated over a long period of monitoring personalized to a subject under observation.

Further, in some embodiments the first and second devices (such as first and second modules attached to first and second patches affixed to a subject) may include one or more orientations sensors and a barometer. The placement of a new patch generally includes a translation component and a rotary component (e.g., rotation about a vector normal to the surface of the skin upon which devices are being placed). Orientation sensors may be used to assist with determining relative rotational changes between applied devices, such as by assessing the gravitational vector read by each kinematic sensor array. The relative rotational changes may be determined by reading rotational vectors associated with movement of a subject as measured simultaneously by each device, by measuring barometric height variation between each device, etc.

Figure 8:
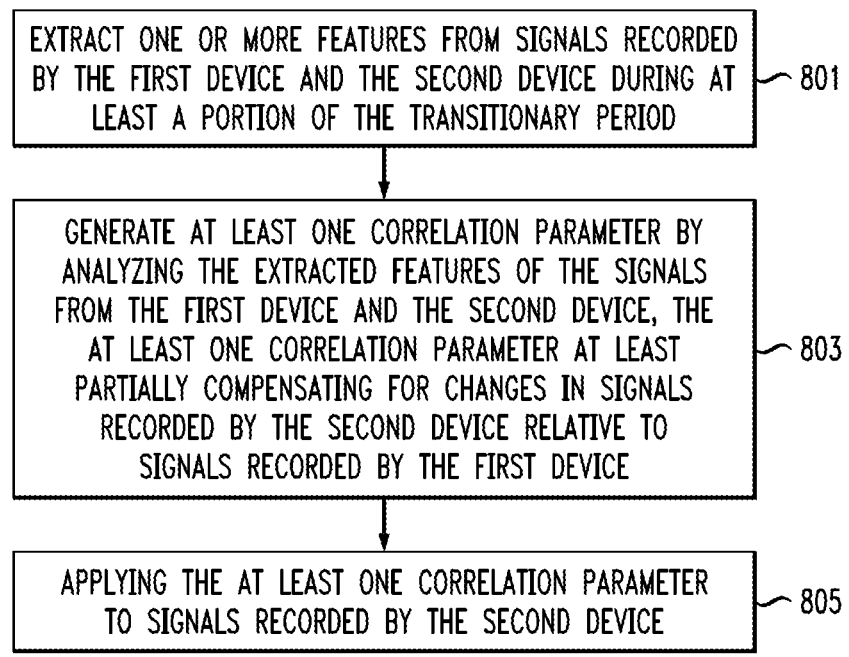
FIG. 8 illustrates a flow diagram of a process for calibration of physiologic parameters, according to an embodiment of the invention.

FIG. 8 shows an example method for synchronization or calibration of devices. In some embodiments, FIG. 8 may be consider an example of the processing of step 609 in FIG. 6, performed during and/or after a transitionary period to calibrate physiologic parameters read by first and second devices. It is important to note that the processing of step 609 in FIG. 6, and the processing in FIG. 8 generally, do not need to be performed in "real-time." In some cases, the calibration or other synchronization of physiologic parameters read by first and second devices may occur while the second device (and possibly the first device) are attached to the subject. Such processing may be performed, for example, by one or more of the first and second devices. For example, such processing may be performed using one or more of the switching components 336-1, 336-2, 356-1 and 356-2 shown and described with respect to FIGS. 3A-3E. Such processing may additionally or alternatively be performed using another device, such as the host device or the patch-module synchronization component 314 of monitoring system 301 shown and described with respect to FIGS. 3A-3E. In some embodiments, wireless transmission of the data from a patch and/or module to a host device or external monitoring system may be expensive, in terms of the power requirements for such transmission. In such cases, it may be preferred to perform such processing locally in one or more of the patches and/or modules.

Synchronization or calibration may be performed in real-time if necessary or desired, such as in monitoring vital signs of a subject in critical care. Synchronization or calibration may also be performed at least partially after one or more of the first and second devices have been removed from a subject, such as in analyzing results of a stress test after the stress test is completed, etc.

The FIG. 8 process begins with step 801, extracting one or more features from signals recorded by the first device and the second device during at least a portion of the transitionary period. The process continues with step 803, generating at least one correlation parameter by analyzing the extracted features of the signals from the first device and the second device. The at least one correlation parameter at least partially compensates for changes in signals recorded by the second device relative to signals recorded by the first device. In step 805, the at least one correlation parameter is applied to signals recorded by the second device.

In some cases, the at least one correlation parameter may provide multi-feature correlation including any combination of the features described herein as desired for a particular application. Some non-limiting examples of multi-feature correlation include combinations of offset and gain, combinations of a noise floor and position correction factor, etc.

While various embodiments are described herein with applying the correlation parameter to signals recorded by one device (i.e., applying the correlation parameter to signals recorded by a second device such that they more closely match signals that would be recorded by a first device), embodiments are not so limited. In some cases, the same or different correlation parameters are applied to signals recorded by the first and second devices, such that the signals recorded by such devices are modified towards a median values or something in between what is measured by each device individually.

Various use cases are described in which a first device is initially attached to a subject and a second device is subsequently attached to the subject. In some cases, the correlation parameters may be generated such that the signals recorded by the second device are adjusted to match that of the first device that was previously attached to and monitoring the subject. This is not a requirement. In some cases, the signals recorded by the first and second devices may be analyzed for some quality measure (e.g., noise performance) and the device with the lower quality measure is adjusted to the device with the higher quality measure. Thus, in some instances the first device previously attached to the subject may have its signals adjusted to match those recorded by the second device subsequently attached to the subject.

Using the FIG. 8 process, continuous long-term monitoring may be provided. For example, signals from the first device may be combined with signals from second device, having the at least one correlation parameter applied thereto, to provide a continuous, calibrated signal covering the first time period, the transitionary period and the second time period.

In the context of location coordination, the extracted features from signals recorded by the first and second devices may include, by way of example, kinematic, postural, electrophysiologic and barometric features. The at least one correlation parameter, in location coordination, may include a relative position and orientation vector, a parametric correlation factor, etc.

In some embodiments, the methods for calibration such as the method described with respect to FIG. 8 may be used to maintain signal continuity, such as maintaining signal continuity during extended monitoring involving electromyography-based physiologic monitoring. In this context, a first device may be applied to a subject and configured so as to monitor EMG at a particular site on the body. The first device may be positioned, for example, such that one or more electrodes includes in the patch (or a patch-module pair) are arranged over target muscle groups specific to a present indication. Some non-limiting examples of such muscle groups include diaphragmatic EMG, bicep EMG, triceps EMG, pelvic muscle EMG, uterine EMC, throat EMG, etc.

The first device, as mentioned above, may be placed on the subject and used to monitor one or more muscle groups for a first time period. At the end of the first time period, a second device may be placed on the subject and the muscle groups may be monitored with both the first and second device for a transitionary period. After the transitionary period, the first device may be removed and the second device may continue to monitor the muscle groups for a second time period. Correlation parameters may be generated so as to coordinate or synchronize the signals recorded by the second device with those recorded by the first device. In the context of measuring EMG, the correlation parameters may be generated by analysis of such recordings as described below. The signals are analyzed to extract features such as action potentials are visible in recordings from both the first and second devices. For such action potentials visible in recordings from both the first and second devise, relative changes in amplitude of the recorded action potentials may be determined. One or more correction factors may be generated, such that the amplitude of action potentials at the first site (e.g., the site at which the first device is attached to the subject) may be estimated from the action potentials at the second site recorded by the second device.

In some embodiments, the methods for calibration such as the method described with respect to FIG. 8 may be used to maintain signal continuity, such as in maintaining continuity of core temperature readings during transition from monitoring with a first device to monitoring with a second device.

In some embodiments, it may be desirable to predict the core temperature of a subject from surface skin temperature recordings. A system in accordance with the present disclosure may be ideal for making such recordings. A device in accordance with the present disclosure may be equipped with a plurality of temperature sensors, as well as an optional humidity and/or an optional barometric sensor. In the device, at least a subset of the temperature sensors may be oriented so as to make essentially intimate thermal contact with the skin of the subject when the device is interfaced therewith, and at least a subset of the temperature sensors may be oriented so as to make intimate thermal contact with the ambient surroundings of the device (e.g., such that a thermal gradient may be established between two or more of the sensors during use). In the device, the local humidity and barometric sensors may be oriented so as to establish local ambient humidity and pressure around the device. In some embodiments, a core temperature of the subject may be estimated based on readings from the skin facing temperature sensor(s) in combination with the thermal gradient. In addition, the optional humidity and barometric sensors may be used to further estimate the thermal conductivity of the ambient surroundings, so as to further improve the core temperature estimation.

In applications, when such a device is nearing the limit of the first monitoring period, a second device including temperature sensors, and optional humidity and/or barometric sensors, may be placed onto the second site of the subject. By nature of the attachment, the second site may include different thermal conductivity with the tissue of the subject as well as to the ambient surroundings from the first site. During a simultaneous monitoring period, the first and second devices may monitor from the respective sensors, and a correlation between the devices may be generated for an estimate of the core temperature of the subject. The correlation may be generated based on a combination of the readings from the separate devices. In aspects, the correlation may be weighted to the device that has the lowest thermal gradient measured between sensors thereupon.

In another embodiment, the first device may be placed at a first site on the body of the subject, the first site being strategically located such that the thermal gradients are naturally minimized in the vicinity thereof (e.g., under an arm, on an inner thigh, in a region protected from the environment by a warm piece of clothing, etc.). The second device may be placed at a site that is more convenient for longer term wear. During a simultaneous monitoring period, the core temperature estimate measured with the second device may be calibrated against the core temperature measurement estimated by the first device. Thus, long-term monitoring may proceed using a device attached to a more convenient site on a subject.

In some embodiments, the methods for calibration such as the method described with respect to FIG. 8 may be used to obviate a need for calibrating a new device to a subject when transitioning from monitoring with a first device to monitoring with a second device. In some cases, when a first device is attached to a subject for monitoring, there may be various calibration processes performed to obtain reliable signals for one or more physiologic parameters, such as eliminating noise or interference. This process may be difficult and/or time consuming. By calculating correlation parameters as described, it may be possible to avoid the need for such calibration of the second device to the subject—replacing a relatively expensive (in terms of time, power and/or computing resources) calibration of device-to-subject with a comparatively inexpensive (in terms of time, power and/or computing resources) device-to-device calibration. Such device-to-subject calibration, for example, may be particularly useful for anesthesia monitoring devices.

In some embodiments, the method may be applied to the continuous monitoring of one or more targeted muscle groups of a subject (e.g., applied to an electromyographic monitoring session). In some embodiments, a first device may be attached to a subject such that one or more electrodes thereupon are oriented in the vicinity of the target muscle group(s). During a first monitoring period, the target muscle (s) of the subject may be activated with varying degrees of exertion, the first device monitoring such activity. During such monitoring the maximum levels of exertion, the relationship of exertion to fatigue, and the like of the target muscle(s) may be determined from the recorded signal(s). To continue monitoring over a period of time, a second device may be placed near to the first device, with one or more electrodes thereupon oriented in the vicinity of the target muscle group(s). During a simultaneous monitoring period, the first and second devices may monitor the target muscle(s) and potentially adjacent muscle group(s). The recorded signals from each device may be simultaneously monitored and compared during the simultaneous monitoring period. During the monitoring period, the target muscle group(s) as well as adjacent muscle groups may be activated, as part of natural movement, or as part of a structured routine. During such movements, the recorded signals may be compared so as to determine overlap of the target muscle group(s), to determine the common muscle group contributions, site unique muscle contributions, and the like.

In some embodiments, one or more feature extraction algorithms may be applied to the signals recorded using the first and second devices, so as to compare them more precisely. In one non-limiting example, a nonlinear transform may be applied to the signals, so as to construct a temporal envelop, and/or a temporal mean therefrom. As various muscle groups are activated, the temporal envelop may be more similar or less similar between the signals obtained from the adjacently placed devices. Furthermore, individual action potentials may be correlated with each other due to the simultaneous nature of the monitoring (i.e., capture of activity associated with specific muscle fibers as recorded from the perspective of each device). To demonstrate the approach, a first device was applied over the flexor digitorum profundus muscle of the left arm of a subject. After a first monitoring period, a second device was placed over the same muscle group, positioned beside the first device closer to the flexor pollicus longus of the left arm of the subject. Before removal of the first device, a period of simultaneous monitoring was performed with both devices in place on the arm of the subject. The signals obtained during this period are used to correct the exertion magnitude of the second device with respect to the first device so as to correlate that muscle activity during a continued monitoring period as measured by the two devices.

Figure 9B:
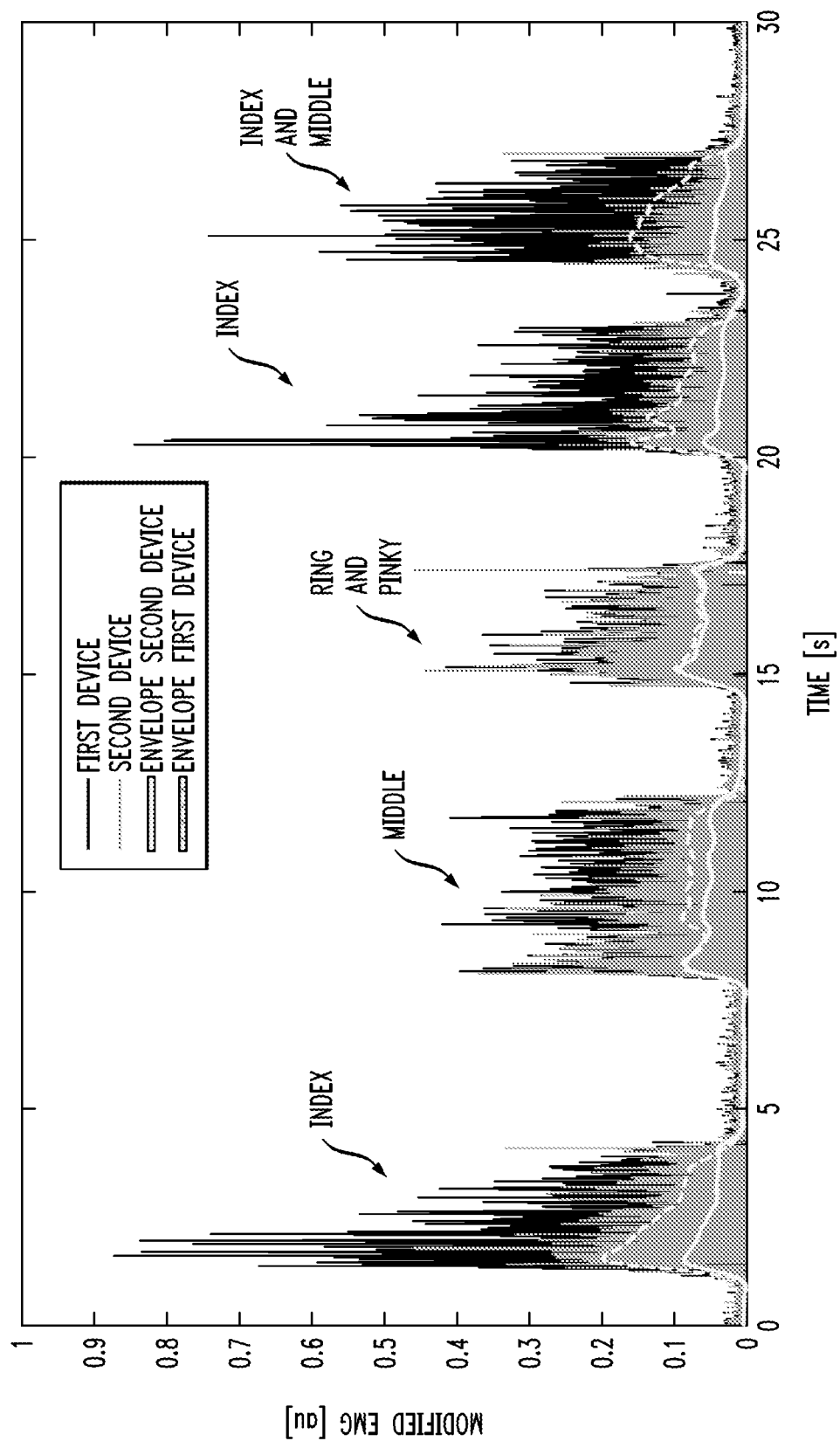

During the monitoring period, the fingers of the subject were flexed in sequence while the monitoring was performed (i.e., fingers were brought into contact with the thumb as labeled in the figures). FIGS. 9A and 9B show plots of the signals obtained from the first and second devices. FIG. 9A shows raw data of signals obtained from the first and second devices, while FIG. 9B shows a plot of the raw data following nonlinear transforms as described above. For example, FIG. 9B shows the raw data after the signals from the first devices are rectified using a square-square root function, and shows the envelopes for the first and second devices obtained by passing such signals through a low-pass filter. It can be seen that the correlation between the EMG envelopes of the recorded signals from the first and second devices was most similar when the pinky and ring fingers were flexed and most different when the index finger was flexed. During the flexion when the signals are most similar (ring and pinky finger flexion), the amplitudes between the recordings can be correlated by adjusting the amplitude of the second signal to match that of the first signal. In some embodiments, more sophisticated approaches to analyzing, matching, and correlating the signals may be performed, including matching particular action potentials against each other that are occurring essentially at the same instant in time (e.g., as determined over a relatively short timescale), matching clusters of signal, analyzing and comparing the frequency spectrums of the signals over a period of time, and the like. The approach may be advantageous due to the ability to perform simultaneous recording of the signals. The same physiologic events may be analyzed from the perspective of each device, thus allowing for the correlation to occur without questioning the source of the activity. Various other approaches, including more sophisticated approaches, may be used in some embodiments for generating correlations, extracting muscle activity information associated with particular muscle group(s), and the like from simultaneously obtained EMGs.

In some embodiments, the methods for calibration such as the method described with respect to FIG. 8 may be used to maintain signal continuity, such as in maintaining consistency of bioimpedance readings measured by a first device at a first site on a subject with bioimpedance measured by a second device at a second site on the subject.

In some embodiments, the methods described herein may be applied to one or more bioimpedance readings, generally associated with a local measure of water content in the adjacent tissues of the subject at the site of a measurement. Such measurements may be suitable for assessing thoracic water content, interstitial fluid load, limb water content, or the like from nearby tissues. In general, such measurements may be made at frequencies over the range of 0.01 Hz to 5 GHz, and may be spread spectrum, single tone, or the like. The tissue impedance may have different relationships to water content at different frequencies. The absolute value of such readings may be prone to wander, varying with the impedance of the electrode-tissue interface, the dermal impedance of the tissues, movement, posture, location of the device on the body of the subject, and the like.

In some embodiments, a hot-swapping approach may be used to minimize some of these effects so as to improve long-term monitoring of the bioimpedance of the subject at one or more sites thereupon. In one non-limiting application, a first device is placed at a site on the chest of a subject, the device equipped with at least one electrode configuration for measuring a bioimpedance of the subject during use. A second device is placed at a site on the leg of the subject, the device equipped with at least one electrode configuration for measuring bioimpedance of the subject during use. Both devices are equipped with one or more kinematic sensors that are suitable for measuring relative height of the devices in a gravitational field, orientation in a gravitational field, etc.

The devices may be configured to simultaneously measure bioimpedance at the plurality of sites while the subject undergoes a daily routine, during a workout, during an orthostatic tilt test, while sleeping, while sitting, or the like. During such testing, the bioimpedance measured at the devices may change in combination with postural changes in the subject, with consumption of certain foods, with consumption of beverages, during or after exercise, during periods of stasis, or the like. The relative changes, and in particular, the differential changes in the bioimpedance readings may correlate with redistribution of the water load in the subject over time. In one non-limiting example, a pair of devices on a subject may monitor a bioimpedance at 1 kHz of approximately 50 ohm (Ω), with the actual value being relatively steady but with considerably different offset from placement to placement due to device-subject interactions and tissue impedance variation. When the subject performs a postural change (e.g., getting out of/into bed, sitting down, standing up, walking, walking up stairs, etc.), the interstitial fluid load in the subject may (slowly) redistribute to accommodate the new posture. In a normotensive subject or in a subject with relatively normal interstitial water load, the ratio between the lower limb bioimpedance and thoracic bioimpedance may increase when changing posture from a lying down to a standing state. In a subject with high interstitial fluid load, the change may be much more pronounced, and if a subject is suffering from orthostatic hypotension, the changes may be far less than in the normotensive subject. Such a ratio as measured in conjunction with the postural data along with contextual data about the subject's habits, may be useful for monitoring long-term changes in interstitial fluid of the subject, and progression of heart disease, and/or hydration level.

In some embodiments, in order to perform long-term monitoring of the subject, a method as described herein, may be advantageous for maintaining a strong correlation between bioimpedance readings when swapping out either of the devices for new devices. In such an example, the new device(s) may be placed in the vicinity of the old device(s) and a period of simultaneous measuring may begin. During the period of simultaneous monitoring, the offset in the bioimpedance measurements, the correlation in the spectral changes in the bioimpedance, as well as other characteristics of the bioimpedance measurements may be analyzed and compared during a routine, a daily routine, etc. by the subject. Thus the bioimpedance measurements may be captured by the devices during a series of postural changes, movements, and activities performed by the subject. Once a correlation is achieved, the method may include an indicator signaling to the subject and/or a caregiver that one or more of the old devices may be removed and monitoring may continue with the new devices.

In some embodiments, the subject may perform one or more maneuvers during the simultaneous monitoring period, such as a tilt test, lying in bed, sitting in a chair, getting out of bed, walking around a room, running on a treadmill, driving in a car, eating a meal, etc. Such monitoring during the routine may provide key differential data from the unique perpectives of the simultaneously monitoring devices, so as to elucidate the overall water load of the subject and changes therein (in terms of the distribution of water, as well as to the overall water load, and changes therein) over time.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:
1. An apparatus comprising:
a memory; and
a processor coupled to the memory;
the processor being configured:

to obtain monitoring data recorded by a first device and a second device, the first device being attached to a subject at a first site and the second device being attached to the subject at a second site different than the first site, the monitoring data comprising a first set of one or more signals associated with at least one physiological parameter of the subject obtained from the monitoring data recorded by the first device and a second set of one or more signals associated with said at least one physiological parameter of the subject obtained from the monitoring data recorded by the second device;

to extract, from the monitored data, one or more features of the first set of one or more signals recorded by the first device and the second set of one or more signals recorded by the second device during a transitionary period when the first device and the second device are simultaneously monitoring said at least one physiological parameter of the subject;

to generate at least one correlation parameter by analyzing the extracted features of the first set of one or more signals recorded by the first device and the second set of one or more signals recorded by the second device for at least a portion of the transitionary period, said at least one correlation parameter when applied to the second set of one or more signals recorded by the second device at least partially compensating for changes in the second set of one or more signals recorded by the second device relative to the first set of one or more signals recorded by the first device; and to apply said at least one correlation parameter to the second set of one or more signals recorded by the second device;

wherein generating said at least one correlation parameter comprises:

correlating changes in one or more of the extracted features of the first set of one or more signals recorded by the first device with corresponding extracted features of the second set of one or more signals recorded by the second device during at least a portion of the transitionary period;

identifying differences between the extracted features of the first set of one or more signals recorded by the second device and the extracted features of the second set of one or more signals recorded by the first device for the correlated changes; and generating said at least one correlation parameter for application to the second set of one or more signals recorded by the second device that offsets at least a portion of the identified differences.

2. The apparatus of claim 1, wherein said at least one correlation parameter at least partially compensates for changes in the first set of one or more signals recorded by the first device and the second set of one or more signals recorded by the second device relative to one another resulting from one or more of:

differences in locations of the first site and the second site;

differences in orientations of the first device and the second device;

differences in tissue properties at the first site and the second site;

differences in coupling of the first device and the second device at the first site and the second site, respectively;

differences in bias pressure in the coupling of the first device and the second device at the first site and the second site, respectively; and differences in electrical and mechanical properties of the first device and the second device.

3. The apparatus of claim 1, wherein said at least one correlation parameter at least partially compensates for changes in the first set of one or more signals recorded by the first device and the second set of one or more signals recorded by the second device relative to one another resulting from one or more of:

differences in magnitudes of physiologic signals recorded by the first device and the second device;

phase delays between physiologic signals recorded at the first site and the second site;

differences in character of the physiologic signals recorded at the first site and the second site;

changes in action potentials of the physiologic signals recorded at the first site and the second site;

changes in offsets of physiologic signals recorded at the first site and the second site; and changes in frequency spectral content of the physiologic signals recorded at the first site and the second site.

4. The apparatus of claim 1, wherein said at least one correlation parameter comprises at least one of a transfer function and a correction factor.

5. The apparatus of claim 1, wherein the correlated changes are associated with one or more designated changes in the subject.

6. The apparatus of claim 5, wherein the one or more designated changes in the subject comprise changes in one or more of: activity level, posture and movement of the subject or an aspect thereof.

7. The apparatus of claim 1, wherein said at least one correlation parameter comprises a translation component and a rotary component offsetting a location difference between the first site and the second site.

8. The apparatus of claim 7, wherein the rotary component represents rotation about a vector normal to a surface of the subject, the rotary component being obtained utilizing one or more orientation sensors and a barometer in the first device and the second device, and wherein rotational changes are determined by assessing gravitational vectors read by kinematic sensor arrays in the first device and the second device and by measuring barometric height variation between the first device and the second device.

9. The apparatus of claim 1, wherein said at least one physiologic parameter comprises at least one electromyography (EMG) measurement, and generating said at least one correlation parameter comprises:

extracting action potential features from a first set of one or more EMG signals recorded by the first device and a second set of one or more EMG signals recorded by the second device;

correlating changes in one or more of the action potential features of the first set of one or more EMG signals recorded by the first device with corresponding action potential features of the second set of one or more EMG signals recorded by the second device during at least a portion of the transitionary period;

identifying one or more action potentials visible in the first set of one or more EMG signals recorded by the first device and the second set of one or more EMG signals recorded by the second device during said portion of the transitionary period;

determining differences between amplitude of the one or more action potentials visible in the first set of one or more EMG signals recorded by the first device and the second set of one or more EMG signals recorded by the second device during said portion of the transitionary period; and generating said at least one correlation parameter by generating one or more correction factors that adjust the amplitude of the one or more action potentials in the second set of one or more EMG signals recorded by the second device so as to estimate an amplitude of action potentials that would be recorded by the first device.

10. The apparatus of claim 1, wherein said at least one physiologic parameter comprises a core temperature measurement, and generating said at least one correlation parameter comprises:

extracting, from one or more sensors of each of the first device and the second device, a corresponding thermal gradient measured based on comparisons of sensor readings from a first subset of the sensors oriented to make thermal contact with the subject with sensor readings from a second subset of the sensors oriented to make thermal contact with ambient surroundings of the first and second devices;

estimating core temperature readings of the subject based on temperature readings from the first subset of sensors of the first and second devices and the corresponding thermal gradients;

correlating changes in core temperature readings from the first device and the second device during at least a portion of the transitionary period; and generating said at least one correlation parameter by combining the correlated changes in core temperature readings of the subject from the first device and the second device.

11. The apparatus of claim 1, wherein said at least one physiologic parameter comprises a bioimpedance measurement, and generating said at least one correlation parameter comprises:

extracting local measures of water content from a first set of one or more bioimpedance signals recorded by the first device and a second set of one or more bioimpedance signals recorded by the second device;

correlating changes in the local measures of water content recorded by the first device with corresponding local measures of water content recorded by the second device during at least a portion of the transitionary period;

identifying differences between the local measures of water content recorded by the second device and the local measures of water content recorded by the first device for the correlated changes; and generating said at least one correlation parameter for application to the second set of one or more bioimpedance signals recorded by the second device that offsets at least a portion of the identified differences.

12. An apparatus comprising:
a memory; and
a processor coupled to the memory;
the processor being configured:
to obtain monitoring data recorded by a first device and a second device, the first device being attached to a subject at a first site and the second device being attached to the subject at a second site different than the first site, the monitoring data comprising a first set of one or more signals associated with at least one physiological parameter of the subject obtained from the monitoring data recorded by the first device and a second set of one or more signals associated with said at least one physiological parameter of the subject obtained from the monitoring data recorded by the second device;

to extract, from the monitored data, one or more features of the first set of one or more signals recorded by the first device and the second set of one or more signals recorded by the second device during a transitionary period when the first device and the second device are simultaneously monitoring said at least one physiological parameter of the subject to generate at least one correlation parameter by analyzing the extracted features of the first set of one or more signals recorded by the first device and the second set of one or more signals recorded by the second device for at least a portion of the transitionary period, said at least one correlation parameter when applied to the second set of one or more signals recorded by the second device at least partially compensating for changes in the second set of one or more signals recorded by the second device relative to the first set of one or more signals recorded by the first device; and to apply said at least one correlation parameter to the second set of one or more signals recorded by the second device;

wherein said at least one physiologic parameter comprises an electrocardiogram (ECG) measurement, and generating said at least one correlation parameter comprises:

extracting wave component features from a first set of one or more ECG signals recorded by the first device and a second set of one or more ECG signals recorded by the second device;

correlating changes in one or more of the wave component features of the first set of one or more ECG signals recorded by the first device with corresponding wave component features of the second set of one or more ECG signals recorded by the second device during at least a portion of the transitionary period;

identifying differences between one or more of the wave component features of the second set of one or more ECG signals recorded by the second device and one or more of the wave component features of the first set of one or more ECG signals recorded by the first device for the correlated changes; and generating said at least one correlation parameter for application to the second set of one or more ECG signals recorded by the second device that offsets at least a portion of the identified differences.

13. The apparatus of claim 12, wherein correlating changes in one or more of the wave component features of the first set of one or more ECG signals obtained by the first device with corresponding wave component features of the second set of one or more ECG signals obtained by the second device is performed on a first average of the first set of one or more ECG signal recorded by the first device and a second average of the second set of one or more ECG signals recorded by the second device during at least a portion of the transitionary period.

14. A non-transitory processor-readable storage medium having stored therein program code of one or more software programs, wherein the program code when executed by at least one processing device causes said at least one processing device:

to obtain monitoring data recorded by a first device and a second device, the first device being attached to a subject at a first site and the second device being attached to the subject at a second site different than the first site, the monitoring data comprising a first set of one or more signals associated with at least one physiological parameter of the subject obtained from the monitoring data recorded by the first device and a second set of one or more signals associated with said at least one physiological parameter of the subject obtained from the monitoring data recorded by the second device;

to extract, from the monitored data, one or more features of the first set of one or more signals recorded by the first device and the second set of one or more signals recorded by the second device during a transitionary period when the first device and the second device are simultaneously monitoring said at least one physiological parameter of the subject;

to generate at least one correlation parameter by analyzing the extracted features of the first set of one or more signals recorded by the first device and the second set of one or more signals recorded by the second device for at least a portion of the transitionary period, said at least one correlation parameter when applied to the second set of one or more signals recorded by the second device at least partially compensating for changes in the second set of one or more signals recorded by the second device relative to the first set of one or more signals recorded by the first device; and to apply said at least one correlation parameter to the second set of one or more signals recorded by the second device;

wherein generating said at least one correlation parameter comprises:
  correlating changes in one or more of the extracted features of the first set of one or more signals recorded by the first device with corresponding extracted features of the second set of one or more signals recorded by the second device during at least a portion of the transitionary period;
  identifying differences between the extracted features of the first set of one or more signals recorded by the second device and the extracted features of the second set of one or more signals recorded by the first device for the correlated changes; and
  generating said at least one correlation parameter for application to the second set of one or more signals recorded by the second device that offsets at least a portion of the identified differences.

15. The non-transitory processor-readable storage medium of claim 14, wherein said at least one correlation parameter at least partially compensates for changes in the first set of one or more signals recorded by the first device and the second set of one or more signals recorded by the second device relative to one another resulting from one or more of:
  differences in locations of the first site and the second site;
  differences in orientations of the first device and the second device;
  differences in tissue properties at the first site and the second site;
  differences in coupling of the first device and the second device at the first site and the second site, respectively;
  differences in bias pressure in the coupling of the first device and the second device at the first site and the second site, respectively; and
  differences in electrical and mechanical properties of the first device and the second device.

16. The non-transitory processor-readable storage medium of claim 14, wherein said at least one correlation parameter at least partially compensates for changes in the first set of one or more signals recorded by the first device and the second set of one or more signals recorded by the second device relative to one another resulting from one or more of:
  differences in magnitudes of physiologic signals recorded by the first device and the second device;
  phase delays between physiologic signals recorded at the first site and the second site;
  differences in character of the physiologic signals recorded at the first site and the second site;
  changes in action potentials of the physiologic signals recorded at the first site and the second site;
  changes in offsets of physiologic signals recorded at the first site and the second site; and
  changes in frequency spectral content of the physiologic signals recorded at the first site and the second site.

17. The non-transitory processor-readable storage medium of claim 14, wherein said at least one physiologic parameter comprises an electrocardiogram (ECG) measurement, and generating said at least one correlation parameter comprises:
  extracting wave component features from a first set of one or more ECG signals recorded by the first device and a second set of one or more ECG signals recorded by the second device;
  correlating changes in one or more of the wave component features of the first set of one or more ECG signals recorded by the first device with corresponding wave component features of the second set of one or more ECG signals recorded by the second device during at least a portion of the transitionary period;
  identifying differences between one or more of the wave component features of the second set of one or more ECG signals recorded by the second device and one or more of the wave component features of the first set of one or more ECG signals recorded by the first device for the correlated changes; and
  generating said at least one correlation parameter for application to the second set of one or more ECG signals recorded by the second device that offsets at least a portion of the identified differences.

18. The non-transitory processor-readable storage medium of claim 17, wherein correlating changes in one or more of the wave component features of the first set of one or more ECG signals obtained by the first device with corresponding wave component features of the second set of one or more ECG signals obtained by the second device is performed on a first average ECG signal recorded by the first device and a second average ECG signal recorded by the second device during at least a portion of the transitionary period.

19. The non-transitory processor-readable storage medium of claim 14, wherein the correlated changes are associated with one or more designated changes in the subject.

20. The non-transitory processor-readable storage medium of claim 19, wherein the one or more designated changes in the subject comprise changes in one or more of: activity level, posture and movement of the subject or an aspect thereof.

* * * * *